US005322847A

United States Patent [19]

Marfat et al.

[11] Patent Number: 5,322,847

[45] Date of Patent: Jun. 21, 1994

[54] AZABENZIMIDAZOLES IN THE TREATMENT OF ASTHMA, ARTHRITIS AND RELATED DISEASES

[75] Inventors: Anthony Marfat, Mystic; James F. Eggler, Stonington, both of Conn.; Michael J. Fray, Wingham, United Kingdom; Kelvin Cooper, Noank, Conn.

[73] Assignee: Pfizer Inc., New York, N.Y.

[21] Appl. No.: 941,108

[22] Filed: Nov. 5, 1992

[51] Int. Cl.[5] .................... A61K 31/44; C07D 471/04

[52] U.S. Cl. .................... 514/303; 514/224.8; 514/225.2; 514/226.2; 544/53; 544/54; 544/55; 546/118

[58] Field of Search .............. 514/224.8, 225.2, 226.2, 514/303; 544/53, 54, 55; 546/118

[56] References Cited

U.S. PATENT DOCUMENTS

| | | | |
|---|---|---|---|
| 4,661,596 | 4/1987 | Kreft, III et al. | 546/152 |
| 4,904,671 | 2/1990 | Cooper | 514/303 |

FOREIGN PATENT DOCUMENTS

| | | |
|---|---|---|
| 0330327 | 8/1989 | European Pat. Off. . |

*Primary Examiner*—Mukund J. Shah
*Assistant Examiner*—Y. N. Gupta
*Attorney, Agent, or Firm*—Peter C. Richardson; Gregg C. Benson; Robert T. Ronau

[57] ABSTRACT

A series of imidazo[4,5-c]pyridines which inhibit platelet activating factor (PAF) and also block leukotriene D4 receptors are useful in treating asthma, arthritis, psoriasis, gastrointestinal distress, myocardial infarction, stroke and shock.

29 Claims, No Drawings

AZABENZIMIDAZOLES IN THE TREATMENT OF ASTHMA, ARTHRITIS AND RELATED DISEASES

CROSS REFERENCE TO RELATED APPLICATIONS

This application is a continuation of International Application PCT/US91/02997, filed 01 May 1991, entitled "Azabenzimidazoles in the Treatment of Asthma, Arthritis and Related Diseases," which is a continuation-in-part of U.S. Ser. No. 07/521,199, filed 09 May 1990, entitled "Azabenzimidazoles in the Treatment of Asthma, Arthritis and Related Diseases" (now abandoned).

BACKGROUND OF THE INVENTION

The present invention is directed to azabenzimidazoles of formula I, which as inhibitors of platelet activating factor (PAF) and of $LTD_4$ receptor binding sites are useful in the treatment or prevention to of asthma, arthritis, psoriasis and a wide range of inflammatory disorders.

Kreft et al., in U.S. Pat. No. 4,661,596, describe compounds which are disubstituted naphthalenes, dihydronaphthalenes or tetralins having the formula

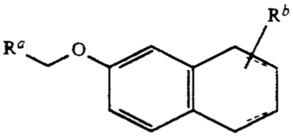

wherein the dotted lines represent optional double bonds, $R^a$ is 2-pyridvl, 2-quinolyl, 2-pyrazinyl, 2-quinoxalinyl, 2-thiazolyl, 2-benzothiazolyl, 2-oxazolyl, 2-benzoxazolyl, 1-alkyl-2-imidazolyl or 1-alkyl-2-benzimidazolyl and $R^b$ is hydroxy, lower alkoxy, lower alkyl or perfluoro alkyl. These compounds inhibit lipoxygenase enzyme and antagonize the effects of leukotriene D4, and so are useful in the prevention and treatment of asthma.

Eggler et al., in copending International application PCT/US87/02745, filed Oct. 19, 1987 have described similarly active compounds, including chromans of the formula

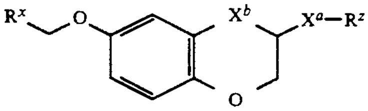

wherein $R^x$ is substantially defined as above, $R^z$ is aryl or heteroaryl, $X^a$ is, for example, oxygen or $CH_2$, and $X^b$ is C=O or CHOH.

More recently, International Application PCT/US89/00975, Publication No. WO 89/08653, describes the preparation of 1-carbamylbenzvlimidazo[4,5-c]pyridines useful as PAF antagonists.

SUMMARY OF THE INVENTION

The present invention comprises compounds of the formula

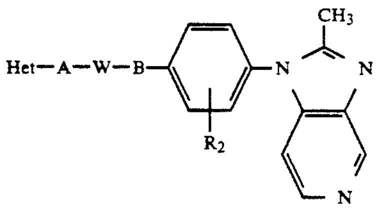

(I)

and a pharmaceutically acceptable acid addition salt thereof, wherein Het is

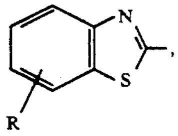
,
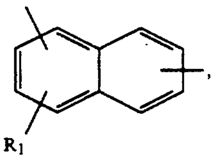
,
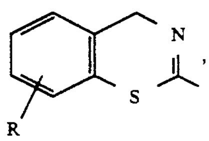
,
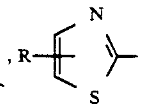
,
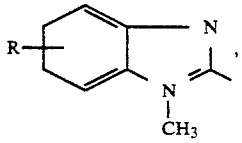
,
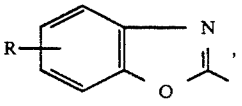
,
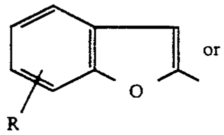
or
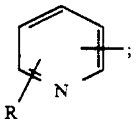
;

A is $-CH_2-O-$, $-CH=CH-$, $-C(CH_3)=CH-$, $-CH_2NH-$, $-C\equiv C-$, $-NHCH_2-$, $-(CH_2)_n-$, $-O-$, $CH_2S(O)_m-$, $-NHCO-$, $-CONH-$ or cycloalkylene having three to six carbon atoms; W is

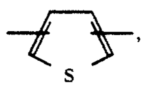
,
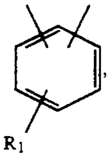
,
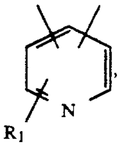
,
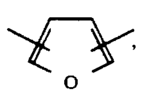
,
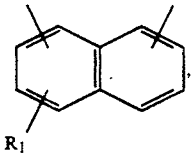
,
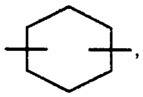
,
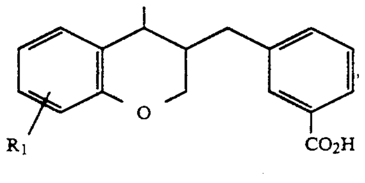
, -continued

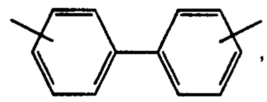, 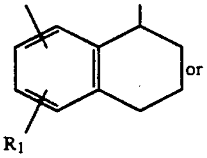 or

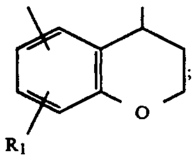;

B is —$NHCH_2$—, —$CH_2O$—, —$CH(CH_3)O$—, —$C(CH_3)_2O$—, —O—, —$(CH_2)_2$—, —$OCH_2$—,

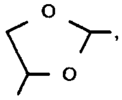, 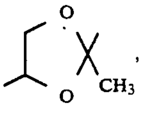,

—$CH_2OCH_2$— or —NHCO—; n is an integer of 1 to 2; m is an integer of 0 to 2; R is hydrogen, fluoro, difluoro, chloro, dichloro, methyl methoxy or trifluoromethy; and $R_1$ and $R_2$ are each hydrogen, fluoro, chloro, methyl, methoxy, acetyl, nitro, amino, carboxy, trifluoromethylsulfonylamino or trifluoromethyl with the proviso that when B is —O—, W is

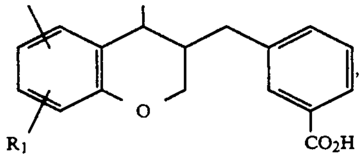,

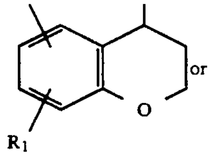 or 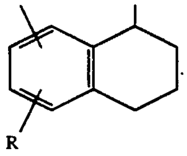.

A preferred group of compounds are those wherein Het is

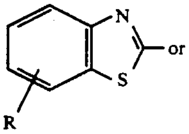 or 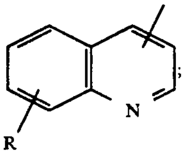;

A is —$CH_2O$— or —CH═CH—; W is

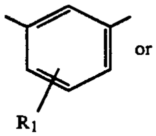 or 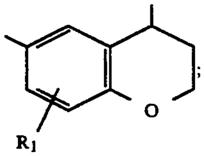;

B is —$CH_2O$—, —$OCH_2$—, —O— or —$CH(CH_3)$—O—; and $R_1$ and $R_2$ are each hydrogen.

Especially preferred within this group are the compounds wherein Het is

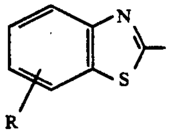

where R is 5-fluoro; A is —CH═CH—; W is

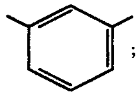;

and B is —$CH_2O$—, wherein Het is

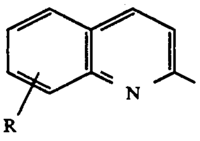

where R is 6-fluoro; A is —CH═CH—; W is

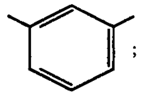;

and B is —$CH_2O$—, wherein Het is

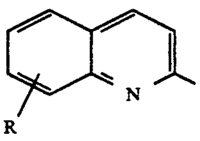

where R is 7-chloro; A is —CH═CH—; W is

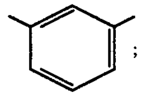;

and B is —$CH_2O$—, wherein Het is

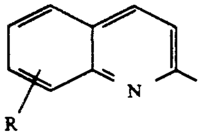

where R is 6-fluoro; A is $—CH_2O—$; W is

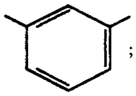
;

and B is $—OCH_2—$, wherein Het is

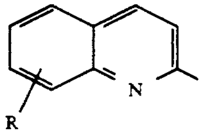

where R is 6-fluoro; A is —CH═CH—; W is

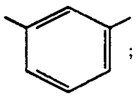
;

and Bis $—CH(CH_3)O—$, wherein Het is

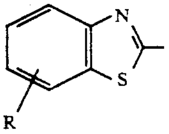

where R is 5-fluoro; A is $—CH_2O$; W is

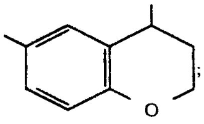
;

and B is —O—, wherein Het is

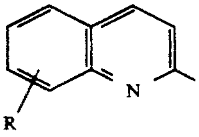

where R is hydrogen; A is $—CH_2O—$; W is

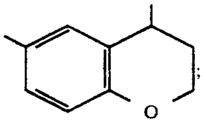
;

and B is —O—, wherein Het is

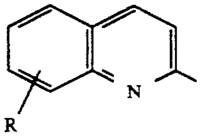

where R is 6-fluoro; A is $—CH_2O—$; W is

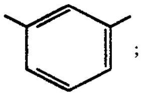
;

and B is $—OCH_2—$, wherein Het is

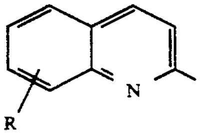

where R is 7-chloro; A is —CH═CH—; W is

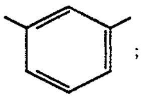
;

and B is $—CH(CH_3)O—$, wherein Het is

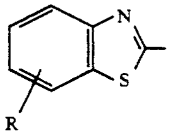

where R is 5-fluoro; A is —CH═CH—; W is

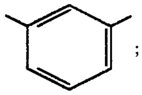
;

and B is $—CH(CH_3)O—$, wherein Het is

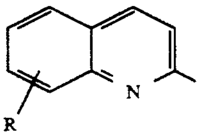

where R is 7-chloro; A is $—CH_2O—$; W is

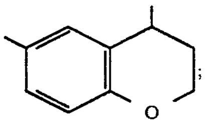
;

and Bis —O—, wherein Het is

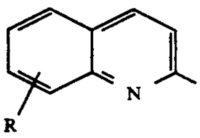

where R is 6-fluoro; A is $—CH_2O—$; W is

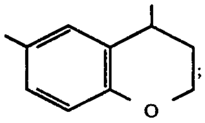
;

and B is —O—, wherein Het is

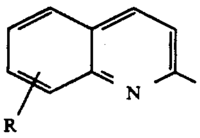

where R is 7-chloro; A is $—CH_2O—$; W is

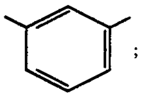
;

and B is $—CH_2O—$, wherein Het is

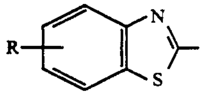

where R is 5-fluoro; A is $—(CH_2)_2—$; W is

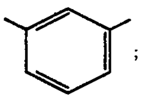
;

and B is $—CH_2O—$, wherein Het is

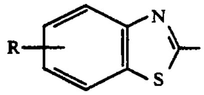

where R is 5,6-difluoro; A is $—CH_2O—$; W is

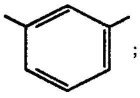
;

and B is $—CH_2O—$ and wherein Het is

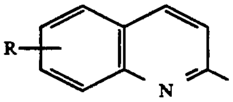

where R is 7-chloro; A is $—(CH_2)_2—$; W is

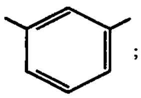
;

and B is $—CH_2O—$, wherein Het is

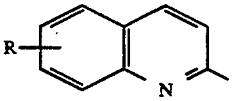

where R is 6-fluoro; A is $—CH_2O—$; W is

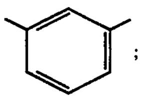
;

and B is $—CH_2O—$, wherein Het is

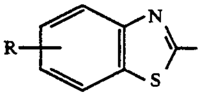

where R is 6-fluoro; A is $—CH_2O—$; W is

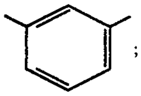
;

and B is $—CH_2O—$.

The present invention includes a pharmaceutical composition for administration to a mammal which comprises a platelet activating factor inhibiting and leukotriene D4 receptor blocking amount of a compound of formula I and a pharmaceutically acceptable carrier.

The present invention also includes a method of inhibiting platelet activating factor and blocking leukotriene D4 receptors in a mammal in need of such treatment which comprises administering to said mammal a platelet activating factor inhibiting and leukotriene D4 receptor blocking amount of a compound of formula I. Preferred is a method wherein the mammal is a human suffering from asthma, arthritis, psoriasis, shock, gastrointestinal ulcers, myocardial infarction or a stroke. The PAF antagonists of the present invention are also useful in preventing rejection in organ transplants.

As previously mentioned, the compounds of the present invention are very unique in that they possess the capacity to both inhibit PAF and block LTD4 receptors. Hence their ability to affect two different pathways to inflammatory disorders makes them extremely useful as medicinal agents.

DETAILED DESCRIPTION OF THE INVENTION

Compounds of the present invention are prepared through the formation of that portion of the structure designated —B— and to a lesser extent by the formation of that portion designated —A—.

When A is —NHCO— or —CONH—, or when B is —NHCO— the compounds of formula I are prepared by coupling the appropriate amine with the requisite acid as follows:

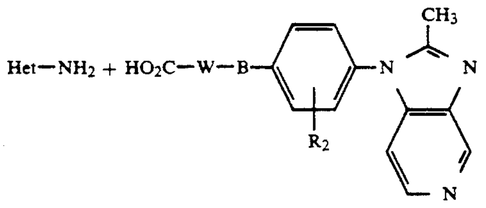

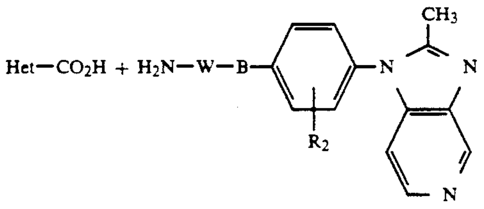

or

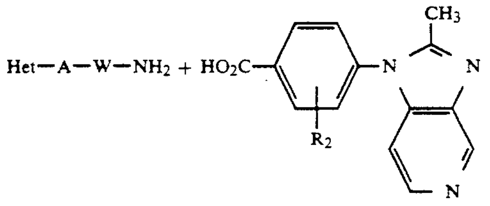

This coupling is carried out by reacting the appropriate acid with approximately an equimolar amount of 1-hydroxybenzotriazole and dicyclohexylcarbodiimide, to form -in situ an activated ester, and subsequently reacting said ester with the desired amine. As one skilled in the art recognizes, a wide variety of activated esters can be used in place of that formed by 1-hydroxybenzotriazole. In addition, diimides other than dicyclohexylcarbodiimide can also be employed with similar results.

The reaction is carried out in a reaction-inert solvent such as dimethylformamide, dimethylsulfoxide or N-methyl-2-pyrrolidone. Reaction time is dependent on reaction temperature. At room temperature the reaction proceeds in 12–72 hours, while under heating at 50°–75° C. the reaction is complete in 30 minutes to a few hours. The product is isolated by quenching the reaction with water followed by extraction with a water immiscible solvent such as ethyl acetate. Purification of the product is by recrystallization, HPLC or flash column chromatography.

Compounds of the present invention wherein B is —$CH_2O$—, —$CH(CH_3)O$—, $C(CH_3)_3)_2O$—, —O— or $\geqq OCH_2$— are prepared by coupling the following fragments:

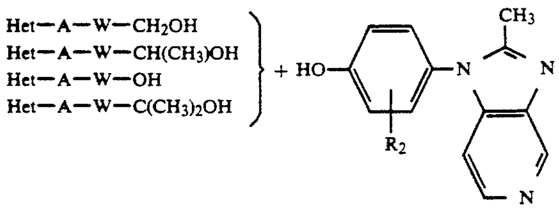

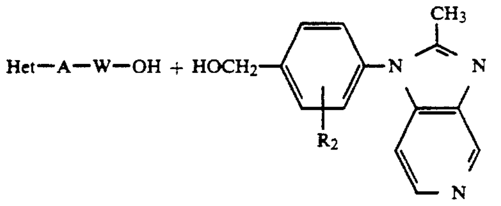

The reaction is conveniently carried out by reacting about equimolar amounts of the two hydroxy reagents with an equimolar amount, plus a 10–20% excess, of triphenylphosphine and an equimolar amount, plus a 50% excess of diethyl azodicarboxylate in a reaction-inert solvent such as dry tetrahydrofuran. The reaction is usually carried out under nitrogen or some inert gas at room temperature. Reaction time under these conditions is about from 12–24 hours, while shorter reaction times can be achieved by gently heating the reaction.

The product can be obtained by removing the reaction solvent and purifying the residue by recrystallization or column chromatography.

Compounds of the present invention where B is —$CH_2O$— or —$CH_2OCH_2$— are prepared by an alkylation reaction employing the following fragments:

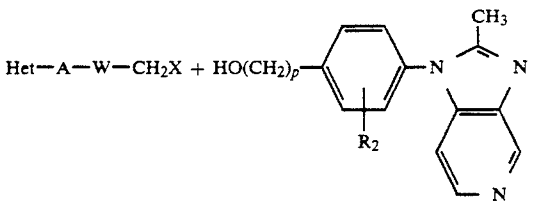

where X=Cl or Br and p is 0 or 1.

The reaction is conducted in a reaction inert water-miscible aprotic solvent such as dimethylformamide, dimethylsulfoxide or N-methyl-2-pyrrolidone. In practice, one mole each of the reacting fragments are combined in an appropriate solvent to which is added three equivalents of an inorganic base such as an alkali metal carbonate, such as potassium carbonate. The reaction, which can be carried out at room temperature, is completed in 0.5 to 5 hours.

Alternately, an alkali metal hydride in a molar amount equal to the alcohol being alkylated can be used in place of the carbonate.

The product is isolated by diluting the reaction mixture with water followed by extraction of the product with a water-immiscible solvent such as ethyl acetate or chloroform. Purification of the product is carried out by recrystallization or chromatography.

Compounds of formula I wherein B is —$(CH_2)_2$— are synthesized by the catalytic reduction of the corresponding olefin. In practice the olefin is shaken with 5% palladium-on-charcoal in a hydrogen atmosphere at a pressure of about 30 ($2.11 \times 10^4$ $Kg/m^2$) psi in a reaction-inert solvent of methanol-tetrahydrofuran at room temperature for 12–24 hours.

The product is isolated filtering the spent catalyst and removing the solvent. The product can be purified by means already mentioned.

Compounds of formula I wherein B is

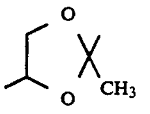

or

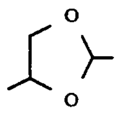

are prepared by reacting the fragments

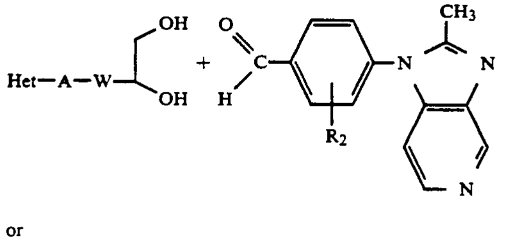

or

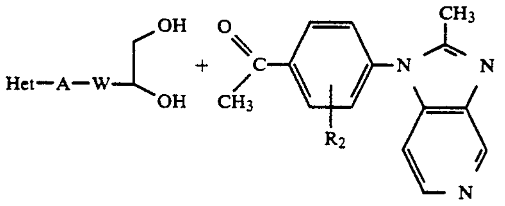

In practice, about equimolar amounts of the requisite diol and carbonyl compounds are combined with a catalytic amount of an acid such as p-toluenesulfonic acid and heated in a reaction-inert solvent which is capable of forming an azeotrope with water, such as benzene or toluene, in such a manner that the water is removed from the reaction in a Dean Stark trap. When the appropriate amount of water has been collected the reaction is complete.

The product is isolated by removing the acid catalyst with a base wash followed by removal of the solvent. Purification is by previously described means.

Compounds of formula I wherein B is $-NHCH_2-$ are prepared by reacting the fragments $Het-A-W-NH_2$ +

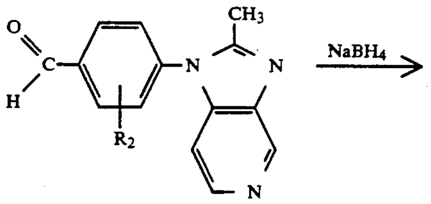

in the presence of a reducing agent such as sodium borohydride or sodium cyanoborohydride.

Experimentally, about equal equivalent amounts of the appropriate amine and aldehyde are combined in a reaction-inert solvent such as methanol containing about an equivalent amount of the reducing agent. The reaction can be conducted at room temperature for a reaction time of several hours.

The product is isolated by the addition of a water immiscible solvent such as ethyl acetate followed by aqueous washings and removal of the appropriate solvent. Purification of the product is by recrystallization or chromatography.

Synthesis of compounds of formula I wherein W is

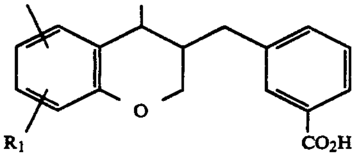

is achieved by base hydrolysis of the corresponding lower alkyl ester. In practice, the ester dissolved in methanol containing at least an equimolar amount of an aqueous alkali metal hydroxide, such as sodium hydroxide, is heated to reflux for 1–2 hours.

The product is isolated by removal of the solvent, addition of water to the residue and precipitation of the product by adjustment of the pH with aqueous acid. Purification is by conventional means.

Compounds of formula I wherein A is a trans olefin can be converted to a cis olefin by photolysis. In practice a sample of the compound of formula I wherein A is a trans olefin in a reaction-inert solvent such as actonitrile/methanol is exposed to natural or artificial light for a period of several days.

The solvent is removed and the residual product wherein A is a cis olefin is purified by conventional means.

As previously indicated, the compounds of formula I form pharmaceutically acceptable acid addition salts. Said pharmaceutically-acceptable acid addition salts include, but are not limited to, those with HCl, HBr, $HNO_3$, $H_2SO_4$, $H_3PO_4$, $CH_3SO_3H$, $p-CH_3C_6H_4SO_3H$, $CH_3CO_2H$, gulconic acid, tartaric acid, maleic acid and succinic acid. In the case of those compounds of the formula (I) which contain a further basic nitrogen, it will, of course, be possible to form diacid addition salts (e.g., the dihydrochloride) as well as the usual monoacid addition salt. Said pharmaceutically-acceptable cationic salts include, but are not limited to, those of sodium, potassium, calcium, magnesium, ammonia, N,N'-dibenzylethylenediamine, N-methylglucamine (meglumine), ethanolamine and diethanolamine.

As one skilled in the art recognizes, compounds of formula I have the potential for containing cis-trans olefins, cis-trans-conformational structures and asymmetric carbon atoms. All these potential isomers are considered within the scope of the present invention.

Concerning the biological activity of the present compounds, it is known that arachidonic acid is metabolized in mammals by means of two distinct pathways, one leading to prostaglandins and thromboxanes, the other to several oxidative products called leukotrienes, which are designated by letter number combinations such as B4, C4, D4 and E4. The first step in this oxidative pathway is the oxidation of arachidonic acid under the influence of 5-lipoxygenase enzyme, an enzyme which is inhibited by many of the compounds (I) of the present invention, thus blocking the synthesis of all leukotrienes. Supplementing this enzyme inhibitory activity is the general ability of the present compounds to antagonize peptidyl leukotrienes (e.g. , block LTD4 receptors), and to antagonize platelet activating factor (e.g., block PAF receptors). These activities themselves provide the mechanism sufficient for the utility of the present compounds in the treatment or prevention of asthma (where LTC4, LTE4, PAF and LTD4 are understood to be mediators), arthritis (where LTD4, LTB4 and PAF are understood to be a mediator in inflammation), psoriasis (where PAF, LTD4 and LTB4 are understood to be a mediator), inflammatory bowel disorder (where leukotrienes and PAF are understood to be mediators), traumatic shock (where PAF and leukotrienes are implicated), stroke (where leukotrienes and PAF are mediators), ulcers (where LTC4 and LTD4 are understood to be mediators) and myocardial infarction (where PAF, LTD4 and LTB4 are understood to be a mediator). For a review concerning leukotrienes, see Bailey et al., *Ann. Reports Med. Chem.* 17, pp. 203-217 (1982).

The in vitro activity of the compounds of the formula (I) is tested as follows. RBL-1 cells, maintained in monolayer form are grown for 1 or 2 days in spinner culture in Minimum Essential Medium (Eagle) with Earl's Salts plus 15% Fetal Bovine Serum supplemented with antibiotic/antimycotic solution (GIBCO). The cells are washed one time with RPMI 1640 (GIBCO) and resuspended in RPMI 1640 plus 1 microM glutathione to a cell density of 1×10 cells/ml. A volume of 0.5 ml of the cell suspension is incubated at 30° C. with 0.001 ml of dimethylsulfoxide solution of drug for 10 minutes. The reaction is started by a simultaneous addition of 0.005 ml (14C)-arachidonic acid in ethanol and 0.002 ml A23187 in dimethylsulfoxide to give final concentrations of 5.0 and 7.6 microM, respectively. After a 5 minute incubation at 30° C., the reaction is stopped by the addition of 0.27 ml acetonitrile/acetic acid (100/0.3) and the media is clarified by centrifugation. Analysis of the product profile is made by a 0.2 ml injection of the clarified supernatant into HPLC. The separation of radioactive products is effected on a radial PAX CN column (5 mm I.D., Waters) with a solvent system of acetonitrile/H 2O/acetic acid (0.1%) with a linear acetonitrile gradient from 35% to 70% over 15 minutes at 1 ml/minute. Quantitation is accomplished with a Berthold Radioactivity Monitor equipped with a built-in integrator and a 0.2 ml flow cell mixing 2.4 ml/minute Omnifluor (NEN) with column effluent. Integration units for each product are calculated at a percentage of total integration units, and then compared to the average control levels. The results are expressed as "Percent of Control" and are plotted vs the log of drug concentration. The $IC_{50}$ values are estimated by graphical inspection.

The platelet activating factor (PAF) receptor assay tests the ability of a compound to compete with radiolabeled PAF for specific PAF receptor sites on rabbit platelet homogenate.

Homogenate Preparation:

Note: All centrifugation is carried out at room temperature.

All tubes and pipets used during homogenate preparation are plastic.

Five hundred milliliters of a rabbit blood mixture is purchased from Rockland, Inc., Gilbertsville, Pa. The blood mixture is 4 parts blood: 1 part 4% sodium citrate (v/v), and is obtained by heart puncture from normal, approximately 8-month old New Zealand white rabbits. The blood mixture is delivered overnight on wet ice (approx. 8° C.).

The blood mixture is centrifuged at 514 g for 10 minutes. The supernatant platelet-rich plasma is gently laid over Ficoll-Paque (Pharmacia) at a ratio of 9 parts plasma:2 parts Ficoll (v/v) The plasma/Ficoll mixture is centrifuged at 856 g for 20 minutes. Located at the interface of the plasma and Ficoll layers, the platelet layer is collected and washed in a buffer containing 150 mM NaCl, 10 mM Tris and 1 mM EDTA (pH 7.5). This mixture is centrifuged at 1926 g for 25 minutes. The resulting pellet is resuspended in the NaCl/Tris/EDTA buffer and centrifuged again (1926 g, 25 minutes). This time the pellet is resuspended in a sodium-free buffer (10 mM Tris, 1 mM EDTA, 5 mM $MgCl_2$ (pH 7.5)) and centrifuged at 1926 g for 25 minutes. The platelet pellet is resuspended in about 10 ml of sodium-free buffer. This suspension is quick-frozen in a methanol/dry ice bath and thawed quickly three times before being frozen again for storage in 1 ml aliquots at −70° C.. Protein concentration of the suspension is determined by a Bio-Rad assay.

Assay Conditions:

Note: All concentrations given are FINAL concentrations in 250 μl.

The following are added to a 12×75 Mm polystyrene tube:

(1) 5 μl of one of the following:
 A. DMSO (to determine total binding)
 B. 1 μl PAF (to determine non-specific binding)
 C. 30 μl—100 μM compound in DMSO
(2) 25 μl 3H-PAF (specific activity 30-60 Ci/mmol) in sodium-free buffer +0.25% bovine serum albumin (BSA) (Approx. 10,000 cpm/25 μl)
(3) 220 μl homogenate preparation (0.1 mg/ml) in sodium-free buffer +0.25% BSA.

The reaction tubes are incubated at 25° C. for 45 minutes. Four ml of cold sodium-free buffer +0.25% BSA are added to each tube. The contents are quickly filtered through a Whatman GF/C filter with a Yeda separation device. The filter is washed 3× with 4 ml sodium-free/BSA buffer. The filter is transferred to a scintillation vial. Ultrafluor scintillation fluid is added. The vial is capped, vortexed and counted for 3H.

Data Calculation and Analysis:

Percent specific binding is calculated using the formula $$\% SB=(X-NSB)/(TB-NSB)$$

where
 X=cpm sample
 NSB=cpm non-specific binding
 TB=cpm total binding

Percent specific binding is graphed as a function of compound concentration. $IC_{50}$ is that concentration at which 50% SB occurs. Alternatively, the $IC_{50}$ is calculated using the logistic dose-response (Hill plot) option of the VAX Biostat utility. The inhibitory constant (Ki) is calculated by using the formula $$Ki=(IC_{50})/[1+(L/Kd)]$$

where
 L=concentration of ligand added (nM)=cpm added/cpm of 1 nM 3H-PAF
 Kd=0.83 nM (dissociation constant)

The leukotriene D4 (LTD4) receptor assay tests the ability of a compound to compete with radiolabeled LTD4 for specific LTD4 receptor sites on guinea pig lung membranes. In this test, normal 3-4 week-old guinea pigs are acclimatized under standard conditions for 3 days prior to being sacrificed. Final animal age: 24–31 days. The guinea pigs are stunned by a blow to the back of the neck, and exsanguinated by cutting the carotid artery. The chest cavity is opened and the lungs are removed, rinsed in 50 mM Tris buffer (pH 7.0) and placed in clean buffer. In this and all subsequent operations, all tissue and buffer are kept on ice throughout the preparation, and all centrifugation is carried out at 4° C. Bronchi and connective tissue are trimmed from the lungs. The tissue is weighed and placed in 50 ml polycarbonate tubes with buffer at a ratio of 1 gm tissue/3 ml buffer. The tissue is homogenized by a Tekmar Tissumizer at full speed for 30 seconds and centrifuged in a Sovall SS-34 rotor at 3250 rpm×15 minutes. The supernatant is centrifuged at 19,000 rpm×10 minutes. The resulting pellet is resuspended in buffer with the Tissumizer at medium speed (position 75) for 10 seconds. The resuspension is again centrifuged at 19,000 rpm×10 minutes. The resulting pellet is resuspended by the Tissumizer at slow speed (position 50) for 10 seconds in 1 ml buffer/g of starting tissue. This final suspension is stirred at 4° C. while aliquoted to polypropylene tubes and stored at −70° C. The following are added to a 12×75 mm polystyrene tube:

(1) 25 microl of one of the following
  A. Dimethylsulfoxide (to determine total binding)
  B. 1 microM LTD4 (to determine non-specific binding)
  C. 30 nanoM—100 microM compound in dimethylsulfoxide
(2) 0.025 ml 3H-LTD4 (specific activity 30–60 Ci/mmol) in 50 mM Tris (pH 7.0)+10 microM L-cysteine (12,000−15,000 cpm/0.025 ml)
(3) 0.2 ml diluted membrane preparation (1 mg/ml) (The preparation is diluted in 50 microM Tris buffer+$MgCl_2$ such that in 200 microl protein, a 10 microM $MgCl_2$ concentration is achieved).

The reaction tubes are incubated at 25° C. for 30 minutes. Four ml of cold Tris buffer+10 microM $MgCl_2$ are added to each tube. The contents are quickly filtered through a Whatman GF/C filter with a Yeda separation device. The filter is washed 3× with 4 ml Tris-$MgCl_2$ buffer. The filter is transferred to a scintillation vial. Ultrafluor scintillation fluid is added. The vial is capped, vortexed and counted for 3 hours. Percent specific binding is calculated using the formula $$\% \; SB=(X-NSB)/(TB-NSB),$$

where
X=cpm sample
NSB=cpm non-specific binding
TB=cpm total binding

Percent specific binding is graphed as a function of compound concentration. $IC_{50}$ is that concentration at which 50% SB occurs. Ki is calculated by using the formula $$Ki=(IC_{50})/[1+(L/Kd)],$$

where
L=concentration of ligand added (microM)=cpm added/cpm of 1 microM 3H-LTD4
Kd=1 microM (dissociation constant)

To evaluate the compounds of the formula (I) in vivo, they are tested by the so-called PAF lethality assay procedure:

Materials:

Mice: CDl males, all approximately the same weight (approximately 26 grams), 12 per group.

Vehicle for oral drug dosing: EES (5% ethanol, 5% emulphor, 90% saline). Stored at room temperature.

Drugs: For routine screening at 50 mg/kg, 20 mg drug is dissolved in 4 ml EES, using sonication in a sonicator bath or grinding in a Ten Broeck grinder to dissolve drug if necessary. If solubility is still a problem, the drug is used as a suspension.

Vehicle for i.v. Injection: Saline with 2.5 mg/ml Bovine Serum Albumin (BSA, Sigma #A4378) and 0.05 mg/ml Propranolol (Sigma #PO884). Prepared fresh daily and kept at room temperature.

Platelet Activating Factor (PAF): A 10 microM stock solution is prepared by dissolving 1 mg PAF (Calbiochem #429460) in 0.18 ml ethanol. This is stored at −20° C. and is diluted in vehicle (see above) the day of use. The concentration of PAF used is calibrated so that when injected at 0.1 ml/10 grams body weight, it will kill approximately 80% of untreated controls. This is usually about 0.028 g/kg (a 1 to 2034 dilution from stock). The solution is prepared in glass containers and is used with glass syringes to minimize surface adhesion by the PAF. It is kept at room temperature.

Positive Control: Phenidone is used at 25 mg/kg (its approximate ED 50).

Method: 45 minutes before PAF injection, mice are treated orally with drug using 0.1 ml/10 grams body weight. Thirty-five to 40 minutes later they are placed under a heat lamp to dilate the caudal vein for PAF injection. PAF is injected i.v. at 0.1 ml/10 grams body weight, and death follows usually within 30 minutes, rarely after 60 minutes. Results are expressed as percent mortality as compared to controls. Because the assay appears to be sensitive to endogenous catecholamines (i.e., beta agonists protect the mice), Propranolol is used to overcome this potential problem. It also helps if the mice are acclimated to the room before testing, and if room noise and temperature are kept moderate and constant. The heat lamp distance should be calibrated so as to permit vasodilation without visible stress to the mice. Fasting the mice should be avoided.

Variations:

1. The time for oral dosing can be changed.

2. Intravenous drug dosing is possible by coinjecting the drug with PAF in the same volume and vehicle as described above. For coinjection, PAF is prepared at twice the desired concentration in saline with BSA and Propranolol as above, and the drug is prepared at twice the desired concentration in the same vehicle. The two preparations are mixed in equal volumes immediately before injection.

For use in the prevention or treatment of asthma, arthritis, psoriasis and gastrointestinal ulcers in a mammal, including man, a compound of the formula (I) is given a PAF inhibiting and leukotriene D4 receptor blocking amount of about 0.5–50 mg/kg/day, in single or divided daily doses. A more preferred dosage range is 2–20 mg/kg/day, although in particular cases, at the discretion of the attending physician, doses outside the broader range may be required. The preferred route of administration is generally oral, but parenteral administration (e.g., intramuscular, intravenous, intradermal) will be preferred in special cases, e.g., where oral absorption is impaired as by disease, or the patient is unable to swallow.

The compounds of the present invention are generally administered in the form of pharmaceutical compositions comprising at least one of the compound of the formula (I), together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

1-[4-[3-(5-Fluorobenzothiazol-2-ylmethoxy)-phenylaminomethyl]phenyl]-2-methyl-1H-imidazo-[4,5-c]pyridine (Het = 5-fluorobenzothiazol-2-yl; A = —$CH_2O$—; W = 1,3-$C_6H_4$; and B = $NHCH_2$)

To a mixture of 371 mg of 3-(5-fluorobenzothiazol-2-ylmethoxy) aniline and 102 mg of sodium cyanoborohydride in 15 ml of methanol and 386 ml of glacial acetic acid was added 3A sieves (400 mg) and the mixture allowed to stir at room temperature for 5 minutes. 1-(p-formylphenyl)-2-methyl-1H-imidazo-[4,5-c]pyridine (384 mg) was added over a period of one minute and the reaction mixture stirred at room temperature for one hour.

The reaction mixture was diluted with ethyl acetate (75 ml) which was then washed with a saturated sodium bicarbonate solution (2×75 ml) and a brine solution (1×75 ml). The solution was separated, dried over sodium sulfate and concentrated in vacuo to give 1.18 g of product as a yellow solid, which was further purified by chromatographing on 75 g of silica using 800 ml of 4% methanol-methylene chloride. The fractions containing the product were combined and concentrated to give 447 mg of a white foam. Recrystallization from diisopropyl ether-methylene chloride gave a pure product, m.p. 151°-152° C.

Anal. Calcd. for $C_{28}H_{22}N_5OSF.\frac{1}{4}H_2O$: C, 66.6; H, 4.6; N, 13.9. Found: C, 66.8; H, 4.3; N, 13.8.

The NMR ($CDCl_3$, 300 MHz) showed absorption at 2.51 (3H), 5.41 (2H) and 4.44 (2H, d, J = 5.6 Hz) delta.

The hydrochloride salt was prepared by treating an ethanol solution of the product with ethyl acetate saturated with hydrogen chloride, m.p. 160° C., dec.

EXAMPLE 2

Employing the procedure of Example 1 and starting with the appropriate reagents, the following compounds were prepared

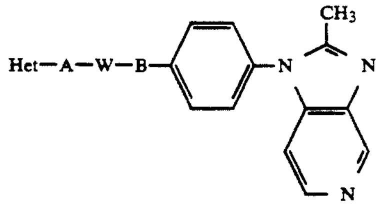

| Het | A | W | B | m.p. °C. |
|---|---|---|---|---|
| 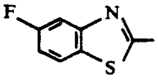 | —$CH_2O$— | 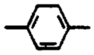 | —$NHCH_2$— | 179-180 |

The NMR ($CDCl_3$, 300 MHz) showed absorption at 2.53 (3H) and 5.39 (2H) delta.

Anal. Calcd. for $C_{28}H_{22}ON_5SF$: C, 67.9; H, 4.5; N, 14.1. Found: C, 67.4; H, 4.6; N, 13.9.

| | | | | |
|---|---|---|---|---|
| 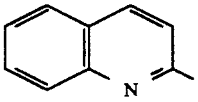 | —$CH_2O$— | 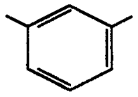 | —$NHCH_2$— | 138-139 |

The NMR ($CDCl_3$, 300 MHz) showed absorption at 2.53 (3H) and 5.32 (2H) delta.

Anal. Calcd. for $C_{30}H_{25}ON_5$: C, 75.7; H, 5.4; N, 14.7 Found: C, 75.9; H, 5.1; N, 14.7.

| | | | | |
|---|---|---|---|---|
| 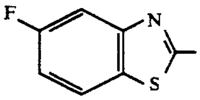 | —CH=CH— | 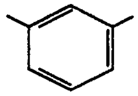 | —$NHCH_2$— | 177-178 |

The NMR ($CDCl_3$, 300 MHz) showed absorption at 2.56 (3H) and 4.54 (2H) delta.

Anal. Calcd. for $C_{29}H_{22}N_5SF$: C, 69.6; H, 4.6; N, 14.0 Found: C, 70.0; H, 4.6; N, 14.0.

EXAMPLE 3

1- (4- [3- (2-Quinol-2-ylmethoxy) phenylmethoxy)-phenyl]-2-methyl-1H-imidazo[4,5-c]pyridine (Het = 2-quinolyl; A = —$CH_2O$—; W = 1,3—$C_6H_4$; and B = —$CH_2O$—)

To a solution consisting of 493 mg of 3-(quinol-2-ylmethoxy)benzyl alcohol, 322 mg of 1-(p-hydroxyphenyl)-2-methyl-1H-imidazo[4,5-c]pyridine and 488 mg of triphenylphosphine in 10 ml of dry tetrahydrofuran was added 388 μl of diethyl azodicarboxylate and the reaction mixture allowed to stir under nitrogen at room temperature overnight. The reaction solvent was removed in vacuo and the residue chromatographed on 80 g of silica using 800 ml each of 2,4 and 6% methanol in methylene chloride (v:v). The fractions containing the product were combined and concentrated to give 522 mg. The product was further purified by recrystallization from ethyl acetate-hexane, 416 mg, m.p. 127°-129° C.

The NMR (300 MHz, $CDCl_3$) showed absorption at 5.12 (2H) and 5.41 (2H) delta.

Anal. Calcd. for $C_{30}H_{24}O_2N_4$: C, 75.7; H, 5.2; N, 11.5 Found: C, 75.2; H, 5.1; H, 11.2.

HRMS: Calcd: 472.1900. Found: 492.1867.

EXAMPLE 4

Starting with the appropriate reagents and using the procedure of Example 3, the following compounds were prepared

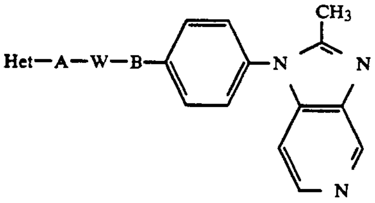

| Het | A | W | B | m.p. °C. |
|---|---|---|---|---|
| 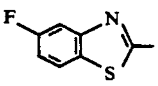 | $-CH_2O-$ | 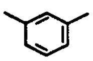 | $-CH_2O-$ | 157-158 |

NMR (300 MHz, $CDCl_3$): 2.55 (3H), 5.14 (2H) and 5.51 (2H) delta.

Anal. Calcd. for $C_{28}H_{21}O_2N_4FS$: C, 67.7; H, 4.3; N, 11.3. Found: C, 67.0; H, 4.0; N, 11.0.

HRMS: Calcd: 496.1396. Found: 496.1369.

| Het | A | W | B | m.p. °C. |
|---|---|---|---|---|
| 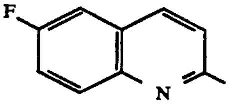 | $-CH_2O-$ | 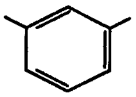 | $-CH_2O-$ | 152-153 |

NMR (300 MHz, $CDCl_3$) 5.12 (2H) and 5.38 (2H) delta.

Anal. Calcd. for $C_{30}H_{23}O_2N_4F$: C, 72.8; H, 4.8; N, 11.3. Found: C, 72.8; H, 4.6; N, 11.3.

Hydrochloride Salt: 200-202

| Het | A | W | B | m.p. °C. |
|---|---|---|---|---|
| 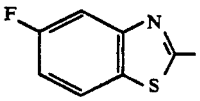 | $-CH_2O-$ | 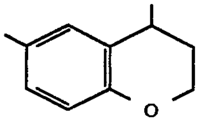 | $-O-$ | 210-211 |

NMR (300 MHz, $CDCl_3$): 2.54 (3H), 4.3 (2H) and 5.41 (2H delta.

Anal. Calcd. for $C_{30}H_{23}N_4O_3SF$: C, 66.3; H, 4.4; N, 10.3. Found: C, 66.4; H, 4.3; N, 10.2.

Hydrochloride Salt: 227-228

| Het | A | W | B | m.p. °C. |
|---|---|---|---|---|
| 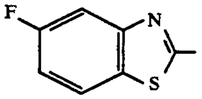 | $-CH_2CH_2-$ | 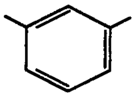 | $-CH_2O-$ | 161-163 |

Anal. Calcd. for $C_{29}H_{23}N_4SOF$: C, 70.4; H, 4.7; N, 11.3. Found: C, 70.0; H, 4.7; N, 11.2.

| Het | A | W | B | m.p. °C. |
|---|---|---|---|---|
| 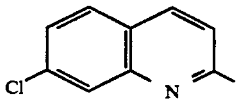 | $-CH_2-CH_2-$ | 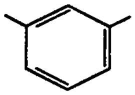 | $-CH_2O-$ | 137-138 |

Anal. Calcd. for $C_{31}H_{25}N_4OCl$: C, 73.7; H, 5.0; N, 11.1. Found: C, 73.6; H, 4.4; N, 10.9.

| Het | A | W | B | m.p. °C. |
|---|---|---|---|---|
| 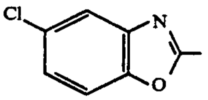 | $-CH=CH-$ (trans) | 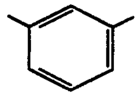 | $-CH_2O-$ | 183-185 |

Anal. Calcd. for $C_{29}H_{21}N_4O_2Cl$: C, 70.7; H, 4.3; N, 11.4. Found: C, 70.6; H, 4.4; N, 10.9.

| Het | A | W | B | m.p. °C. |
|---|---|---|---|---|
| 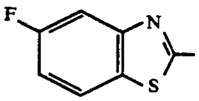 | $-CH_2SO-$ | 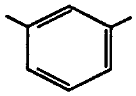 | $-CH_2O-$ | 175 (dec) |

Anal. Calcd. for $C_{28}H_{21}N_4O_2FS_2.HCl.2H_2O$: C, 56.0; H, 4.4; N, 9.3. Found: C, 55.8; H, 4.6; N, 9.1.

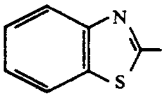 —$CH_2SO_2$— 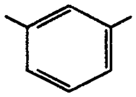 —$CH_2O$— 195 (dec)

Anal. Calcd. for $C_{28}H_{21}N_4O_3FS_2.HCl.2H_2O$ C, 54.5; H, 4.3; N, 9.1. Found: C, 54.3; H, 3.9; N, 9.6.

EXAMPLE 5

1-[4-[3-(5-Fluorobenzothiazol-2-yl-transethenyl)-phenylmethoxylphenyl]-2-methyl-1H-imidazo[4,5-c]pyridine (Het=5-fluorobenzothiazol-2-yl; A=(trans) —CH=CH—; W=1,3 —$C_6H_4$; and B=—$CH_2O$—)

Following the procedure of Example 3 and starting with 406 mg of 3-(5-fluorobenzothiazol-2-ylethenyl)-benzyl alcohol, 320 mg of 1-(p-hydroxyphenyl)-2-methyl-1H-imidazo[4,5-c]pyridine, 410 mg of triphenylphosphine and 268 μl of diethyl azodicarboxylate in 8 ml of dry tetrahydrofuran there was obtained 460 mg of crude product which was recrystallized from diisopropyl ether—methylene chloride, 383 mg, m.p. 197°-199° C.

The NMR (300 MHz, $CDCl_3$) showed absorption at 2.53 (3H) and 5.20 (2H) delta.

Anal. Calcd. for $C_{29}H_{21}ON_4SF$: C, 70.7; H, 4.3; N, 11.4. Found: C, 70.7; H, 4.1; N, 11.4.

The hydrochloride salt of the product was prepared by treating an ethanol solution of the product with ethyl acetate saturated with hydrogen chloride, m.p. 259°-261 C.

EXAMPLE 6

Starting with the appropriate reagents and using the procedure of Example 3, the following analogs were prepared

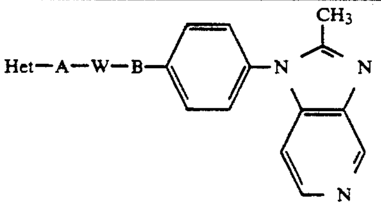

| Het | A | W | B | m.p. °C. |
|---|---|---|---|---|
| 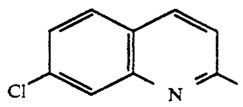 | —CH=CH— (trans) | 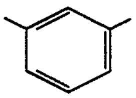 | —$CH_2O$— | 169-170 |

NMR (300 MHz, $CDCl_3$) 2.54 (3H) and 5.20 (2H) delta.

Anal. Calcd. for $C_{31}H_{23}ON_4Cl$: C, 74.0; H, 4.6; N, 11.1. Found: C, 73.8; H, 4.3; N, 11.3.

Hydrochloride Salt: 255-257

Anal. Calcd. for $C_{31}H_{23}ON_4Cl.2HCl$: C, 64.7; H, 4.4; N, 9.7. Found: C, 64.2; H, 4.3; N, 9.5.

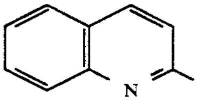 —CH=CH— (trans) 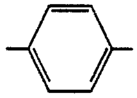 —$CH_2O$— 209

NMR (300 MHz, $CDCl_3$) 2.54 (3H) and 5.18 (2H) delta.

Anal. Calcd. for $C_{31}H_{24}ON_4$: C, 78.7; H, 5.2; N, 11.9. Found: C, 78.5; H, 5.0; N, 11.7.

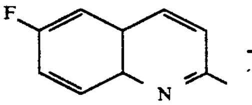 —CH=CH— (trans) 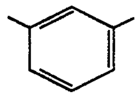 —$CH_2O$— 177-178

NMR (300 MHz, $CDCl_3$) 2.55 (3H) and 5.20 (2H) delta.

Anal. Calcd. for $C_{31}H_{23}ON_4F$: C, 75.8; H, 4.8; N, 11.4. Found: C, 75.6; H, 4.6; N, 11.2.

Hydrochloride Salt 266-268

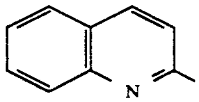 —CH=CH— (trans) 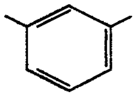 —$CH_2O$— 95-100

NMR (300 MHz, $CDCl_3$) 2.52 (3H) delta. HRMS: Calcd.: 468.1952. Found: 468.1961.

| | | | | |
|---|---|---|---|---|
| 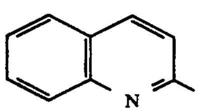 | —CH=CH— (trans) | 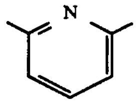 | —$CH_2O$— | 112-115 |

NMR (300 MHz, $CDCl_3$) 2.53 (3H and 5.33 (2H) delta. HRMS: Calcd: 469.1903. Found: 469.1886.

| | | | | |
|---|---|---|---|---|
| 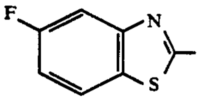 | —CH=CH— (trans) | 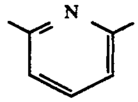 | —$CH_2O$— | 205-206 |

NMR (300 MHz, $CDCl_3$) 2.52 (3H) and 5.32 (2H) delta.

Anal. Calcd. for $C_{28}H_{20}N_5OSF$: C, 67.5; H, 4.2; N, 14.1. Found: C, 67.5; H, 5.3; N, 13.7.

| | | | | |
|---|---|---|---|---|
| 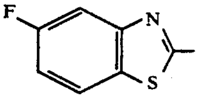 | $CH_3$ —C=CH— (trans) | 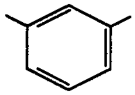 | —$CH_2O$— | 165-166 |

NMR (300 MHz, $CDCl_3$) 2.52 (3H) and 5.20 (2H) delta.

Anal. Calcd. for $C_{30}H_{23}N_4OSF$: C, 71.1; H, 4.6; N, 11.1. Found: C, 70.7; H, 4.1; N, 10.8.

| | | | | |
|---|---|---|---|---|
| 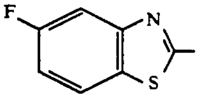 | —CH=CH— (trans) | 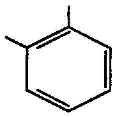 | —$CH_2O$— | 160-161 |

NMR (300 MHz, $CDCl_3$) 5.32 (s, 2H) and 2.52 (s, 3H) delta.

Anal. Calcd. for $C_{29}H_{21}N_4OSF$: C, 70.7; H, 4.3; N, 11.4. Found: C, 70.6; H, 4.1; N, 11.2.

| | | | | |
|---|---|---|---|---|
| 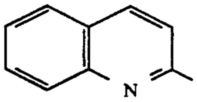 | —$CH_2$—$CH_2$— | 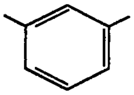 | —$CH_2O$— | 215-220 (HCl) |

NMR (300 MHz, DMSO-$d_6$) 2.55 (3H) and 5.19 (2H) delta.

HRMS: Calcd.: 470.2109. Found: 480.2108.

EXAMPLE 7

1-[4-[3-(6-Fluorobenzothiazol-2-ylmethoxy)phenylmethoxy]phenyl]-2-methyl-1H-imidazo[4,5-c]pyridine (Het=6-fluorobenzothiazol-2-yl; A=$CH_2O$—; W=1,3—$CH_6H_4$; and B=—$CH_2O$—)

Following the procedure of Example 3, 321 mg of the product of Preparation L, 349 mg of triphenylphosphine, 250 mg of the product of Preparation B and 230 μl of diethyl azodicarboxylate in 10 ml of dry tetrahydrofuran gave, after chroatographing on 85 g of silica gel using from 2% methanol—98% methylene chloride (v:v) to 6% methanol—94% methylene chloride (v:v), 273 mg of the titled product, m.p. 137°-138° C.

The NMR (300 MHz, $CDCl_3$) showed absorption at 2.51 (s, 3H), 5.13 (s, 2H) and 5.48 (s, 2H) delta.

Anal. Calcd. for $C_{28}H_{21}N_4O_2FS$: C, 67.7; H, 4.3; H, 11.3 Found: C, 67.4; H, 3.9; N, 11.1.

EXAMPLE 8

Starting with the appropriate reagents and using the procedure of Example 3, the following compounds were prepared:

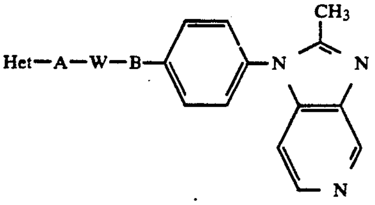

| Het | A | W | B | m.p. °C. |
|---|---|---|---|---|
| 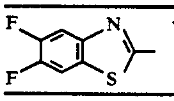 | —$CH_2O$— | 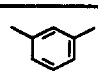 | —$CH_2O$— | 170-171 |

NMR (300 MHz, $CDCl_3$) 2.51 (s, 3H), 5.13 (s, 2H) and 5.48 (s, 2H) delta.

Anal. Calcd. for $C_{28}H_{20}N_4O_2SF_2$: C, 65.4; H, 3.9; N, 10.9. Found: C, 65.1; H, 3.8; N, 10.6.

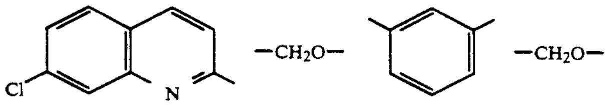

80-85
(dec)

NMR (300 MHz, $CDCl_3$) 2.50 (s, 3H), 5.11 (s, 2H) and 5.39 (s, 2H) delta.

Mass Spec.: Calcd.: 506.4. Found: 506 M+.

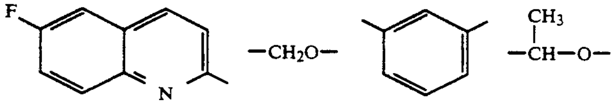

135
(dec)
(2HCl)

NMR (300 MHz, DMSO-$d_6$) 1.58 (d, 3H) and 2.50 (s, 3H) delta.

Anal. Calcd. for $C_{31}H_{25}N_4O_2F.2HCl$: C, 61.6; H, 5.0; N, 9.3. Found: C, 61.7; H, 5.3; N, 9.2.

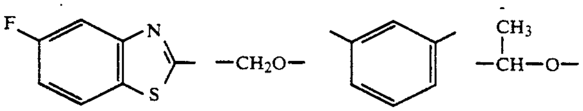

166-168
(HCl)

NMR (300 MHz, DMOS-$d_6$) 1.61 (d, 3H, J=6.3 Hz) and 2.50 (s, 3H) delta.

Mass Spec.: Calcd.: 510.6. Found: 510 M+.

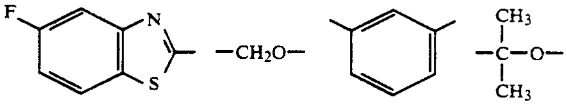

137-139

NMR (300 MHz, $CDCl_3$) 1.78 (s, 6H) and 2.47 (s, 3H) delta.

Mass Spec.: Calcd. 524.6; Found 524+.

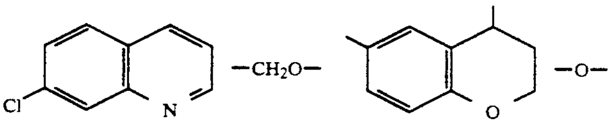

215-216

NMR (300 MHz, $CDCl_3$) 2.54 (s, 3H)

Anal. Calcd. for $C_{32}H_{25}O_3N_4Cl$: C, 70.0; H, 4.6; N, 10.2. Found: C, 69.7; H, 4.4; N, 10.0.

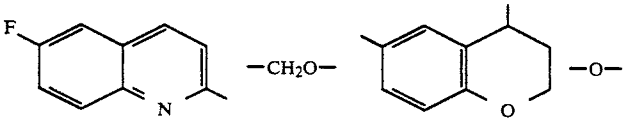

245-246
(2HCl)

NMR (300 MHz, $CDCl_3$) 2.54 (s, 3H) and 5.29 (s, 2H) delta.

Mass Spec.: Calcd. 532.5; Found: 532+.

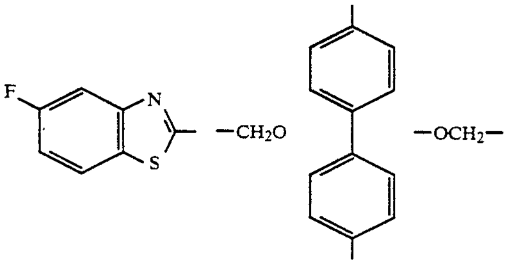

244-246

Anal. Calcd. for $C_{34}H_{25}N_4O_2SF$: C, 71.3; H, 4.4; H, 9.8. Found: C, 70.9; H, 4.1; N, 9.6.

EXAMPLE 9

1-[4-[3-(5-Fluorobenzothiazol-2-ylmethoxy)phenylmethoxymethyl]phenyl)-2-methyl-1H-imidazo-[4,5-c]pyridine hydrochloride (Het=5-fluorobenzo-thiazol-2-yl; A=$-CH_2O$; W=1,3$-C_6H_4$; and B=$-CH_2OCH_2-$)

To a solution of 443 mg of the product of Preparation B in 8 ml of dimethylformamide was added 78 mg of 60% sodium hydride. After stirring for 15 minutes, 650 mg of the product of Preparation P was added, and the reaction mixture stirred for 30 minutes. The reaction was diluted with water and extracted with ethyl acetate. The extracts were washed with water and a brine solution and dried over sodium sulfate. Removal of the solvent gave 830 mg of crude product which was chromatographed on 110 g of silica gel using from 2 to 4 to 6% methanol—98 to 96 to 94% methylene chloride (v:v), to give 113 mg of product.

The product was dissolved in ethyl acetate and treated with a 1N solution of hydrogen chloride in ether, 95.6 mg, m.p. 168°-170° C.

The NMR (300 MHz, DMSO-$d_6$) showed absorption at 2.58 (s, 3H), 4.68 (s, 2H) and 4.63 (s, 2H) delta.

Mass Spec.: Calcd. 510.6; Found: 510+.

In a similar manner, the product of Preparation B and 3-(5-fluorobenzothiazol-2-ylmethylthio)benzylbromide gave 1-[4-[3-(5-fluorobenzothiazol-2-ylmethylthio)-phenylmethoxy]phenyl]-2-methyl-1H-imidazo[4,5-c]pyridine, m.p. 119°-121° C.

The NMR showed absorption at 2.48 (s, 3H), 4.52 (s, 2H) and 5.05 (s, 2H) delta.

EXAMPLE 10

Using the procedure of Example 3, and starting with the requisite starting materials, the following compounds were prepared

| Het | A | W | B | m.p. °C. |
|---|---|---|---|---|
| 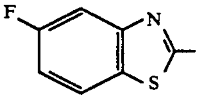 | $-CH_2O-$ | 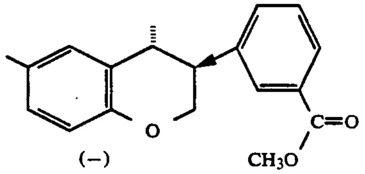 (−) | —O— | 169-170 |

NMR (300 MHz, $CDCl_3$) 2.2 (s, 3H), 3.88 (s, 3H) and 5.42 (s, 2H) delta.

Mass Spec.: Calcd 686.7; Found: 686+.

| | | | | |
|---|---|---|---|---|
| 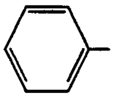 | $-CH=CH-$ (trans) | 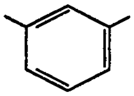 | $-CH_2O-$ | 106-107 |

NMR (300 MHz, $CDCl_3$) 2.52 (s, 3H) and 5.17 (s, 2H) delta.

Anal. Calcd. for $C_{28}H_{23}N_3O$: C, 79.4; H, 5.6; N, 9.9. Found: C, 79.4; H, 5.3; N, 9.7.

| | | | | |
|---|---|---|---|---|
| 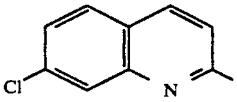 | $-CH=CH-$ (trans) | 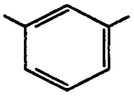 | $-\overset{CH_3}{CH}O-$ | 160-165 (dec) (2HCl) |

NNR (300 MHz, DMSO-$d_6$) 2.52 (s, 3H) and 1.68 (d, 3H, J=6.3 Hz) delta.

Anal. Calcd. for $C_{32}H_{25}N_4OCl.2HCl$: C, 63.2; H, 4.8; N, 9.2. Found: C, 63.2; H, 5.1; N, 8.8.

| | | | | |
|---|---|---|---|---|
| 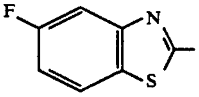 | $-CH=CH-$ (trans) | 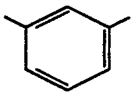 | $-\overset{CH_3}{CH}O-$ | 202-205 (HCl) |

NMR (300 MHz, DMSO-$d_6$) 1.67 (d, 3H, J=6.2 Hz) and 2.51 (s, 3H) delta.

Mass Spec.: Calcd. 506.6. Found 506+.

| | | | | |
|---|---|---|---|---|
| 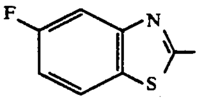 | $-CH=CH-$ (trans) | 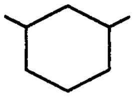 | $-CH_2O-$ | 231-233 |

Anal. Calcd. for $C_{29}H_{27}N_4SOF$: C, 69.9; H, 5.5; N, 11.2. Found: C, 69.2; H, 6.2; N, 11.0.

| | | | | |
|---|---|---|---|---|
| 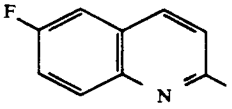 | —CH=CH— (trans) | 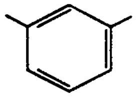 | 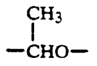 | 190–195 (dec) (HCl) |

NMR (300 MHz, DMSO-$D_6$) HRMS: Calcd.: 500.2014. Found : 500.1946.

EXAMPLE 11 trans-3- (3-Carboxybenzyl) -4- (4-[2-methyl-1H-imidazo[4,5-c]pyrid-1-yl]phenoxy) -6-(5-fluorobenzothiazol-2-ylmethoxy)chroman (Het 5-fluorobenzothiazol-2-yl; A=—$CH_2O$—; W trans-

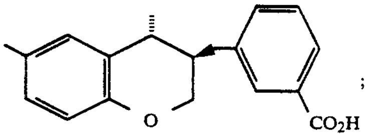 ;

and B = —O—)

To 12 ml of methanol was added 316 mg of the methyl ester of the titled product (Example 10, compound No. 1) and 6 ml of 6N aqueous sodium hydroxide solution and the resulting reaction mixture heated to reflux for 1.5 hours. The methanol was removed in vacuo and the residue poured into 150 ml of water. Ethyl acetate was added to the aqueous solution and the pH adjusted to about 7 with 1N hydrochloric acid. The resulting precipitate was filtered and dried 205 mg, m.p. 251–253.

Anal. Calcd. for $C_{38}H_{29}N_4O_5FS.2H_2O$: C, 64.4; H, 4.7; N, 7.9. Found: C, 64.0; H, 4.2; N, 7.8.

The NMR (300 MHz, DMSO-$d_6$) showed absorption at 2.45 (s, 3H) and 5.55 (s, 2H) delta.

EXAMPLE 12

1-[4-[3-(5-Fluorobenzothiazol-2-yl-cis-ethenyl)phenylmethoxy]phenyl) -2-methyl-1H-imidazo[4,5-c]pyridine (Het=5-fluorobenzothiazol-2-yl; A=(cis) —CH=CH—; W=1,3—$C_6H_4$; and B=—$CH_2O$—)

A solution of 63.7 mg of the product of Example 5 in 4 l of acetonitrile and 2 l of methanol was allowed to stand at room temperature exposed to light for 6 days. The solvent was removed and the product, 65.8 mg, was assayed to about 10% starting material and 90% of the titled product. The residue was purified by chromatographing on 15 g of silica gel to give 50.9 mg of product. A small portion was recrystallized from ethyl acetate—hexane.

HRMS: Calcd.: 492.1422. Found 492.1384.

The NMR (300 MHz, $CDCl_3$) showed absorption at 2.49 (s, 3H) and 5.17 (s, 2H) delta.

EXAMPLE 13

Using the procedure of Example 3 and starting with the appropriate reagents, the following compounds were prepared

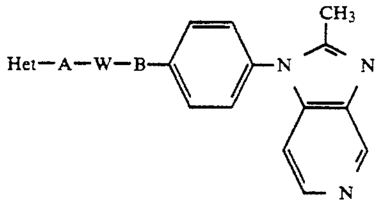

| Het | A | W | B | m.p. °C. |
|---|---|---|---|---|
| 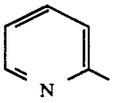 | —CH=CH— (trans) | 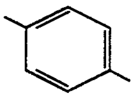 | —$CH_2O$— | 256–258 (2HCl) |

Anal. Calcd. for $C_{27}H_{22}N_4O$: C, 66.0; H, 4.9; N, 11.4. Found: C, 65.7; H, 4.9; N, 11.4.

| | | | | |
|---|---|---|---|---|
| 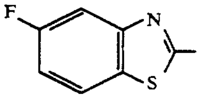 | —CH=CH— (trans) | 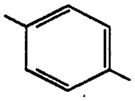 | —$CH_2O$— | 248–250 |

NMR (300 MHz, $CDCl_3$) 2.52 (s, 3H) and 5.10 (s, 2H) delta.

| | | | | |
|---|---|---|---|---|
| 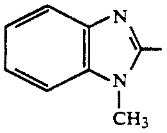 | —CH=CH— (trans) | 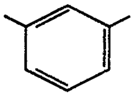 | —$CH_2O$— | 140–142 |

NMR (300 MHz, $CDCl_3$) 2.50 (s, 3H), 3.87 (s, 3H) and 5.17 (s, 2H) delta

Anal. Calcd. for $C_{29}H_{21}N_4SO_2F_3$.HCl: C, 59.7; H, 3.8; N, 9.6. Found: C, 59.4; H, 3.6; N, 9.4.

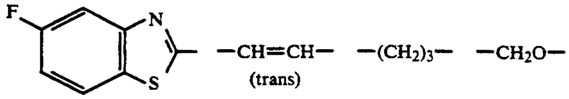

—CH=CH— (trans) —$(CH_2)_3$— —$CH_2O$— 126–128

Anal. Calcd. for $C_{29}N_{21}N_4SOF$: C, 70.7; H, 4.3; N, 11.4. Found: C, 70.5; H, 4.1; N, 11.3.

NMR (300 MHz, $CDCl_3$) 1.80 (m, 2H), 1.90 (m, 2H), 2.42 (q, 2H), 2.48 (s, 3H) and 4.06 (t, 2H) delta.

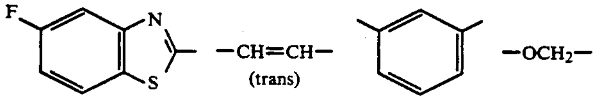

—CH=CH— (trans) —$OCH_2$— 169–171

NMR (300 MHz, $CDCl_3$) 2.57 (s, 3H) and 5.23 (s, 2H) delta.

Anal. Calcd. for $C_{26}H_{23}N_4SOF$: C, 67.3; H, 5.4; N, 11.5. Found: C, 67.6; H, 5.2; N, 11.9.

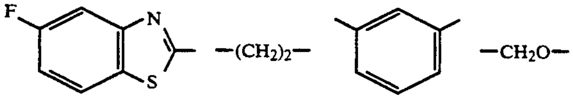

—$(CH_2)_2$— —$CH_2O$— 157–159

Mass Spec. 492+.

NMR (300 MHz, $CDCl_3$) 2.49 (s, 3H), 3.23 (t, 2H),

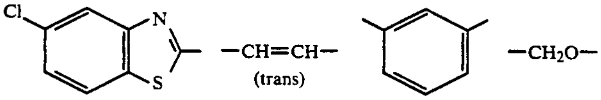

—CH=CH— (trans) —$CH_2O$— 205–207

NMR (300 MHz, $CDCl_3$) 2.5 (s, 3H) and 5.18 (s, 2H) delta.

3.43 (t, 2H) and 5.10 (s, 2H) delta.
HRMS: Calcd.: 494.1577. Found : 494.1579.

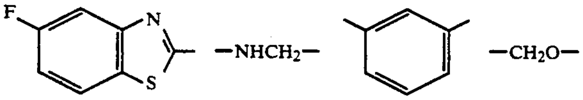

—$NHCH_2$— —$CH_2O$— 207–210

Mass Spec. 509+.

NMR (300 MHz, $CDCl_3$) 2.48 (s, 3H) 4.66 (s, 2H) and

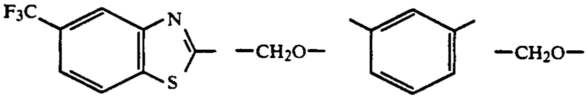

—$CH_2O$— —$CH_2O$— 156–158

NMR (300 MHz, $CDCl_3$) 2.49 (s, 3H), 5.12 (s, 2H) and 5.52 (s, 2H) delta.

5.11 (s, 2H) delta.
HRMS: Calcd.: 509.1316. Found 509.1258.

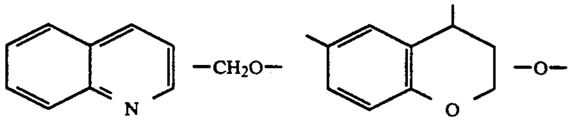

—$CH_2O$— —O— 201–203

Anal. Calcd. for $C_{29}H_{21}N_4SO_2F_3$: C, 63.7; H, 3.9; N, 10.3. Found: C, 63.4; H, 3.9; N, 10.1.
Hydrochloride: 241-243.

NMR (300 MHz, $CDCl_3$) 2.52 (s, 3H) and 5.30 (s, 2H) delta.
Mass Spec. 514+.

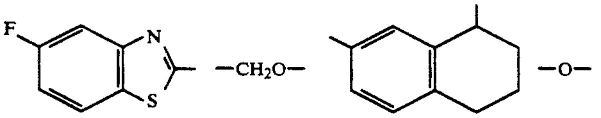 198-200

NMR (300 MHz, $CDCl_3$) 2.54 (s, 3H), 5.44 (s, 2H). Anal. Calcd. for $C_{31}H_{25}N_4SO_2F$: C, 69.4; H, 4.7; N, 10.4. Found: C, 69.0; H, 4.5; N, 10.3.

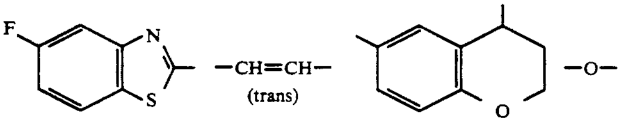 263-265

NMR (300 MHz, $CDCl_3$) 2.35 (m, 2H), 2.54 (s, 3H), 4.37 (m, 2H) , 6.95 (m, 1H) delta.

Mass Spec. 534+.

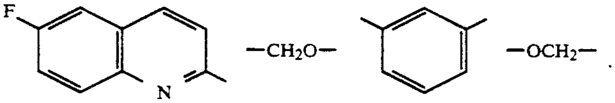 133-135

NMR (300 MHz, $CDCl_3$) 2.50 (s, 3H), 5.10 (s, 2H), 5.32 (s, 2H) delta.

Mass Spec. 490+.

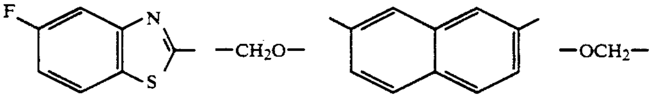 179-181

NMR (300 MHz, $CDCl_3$) 2.48 (s, 3H) , 5.20 (s, 2H) , 5.52 (s, 2H) delta.

Anal. Calcd. for $C_{32}H_{23}N_4SO_2F$: C, 69.0; H, 6.0; N, 10.1. Found: C, 69.8; H, 4.3; N, 10.0.

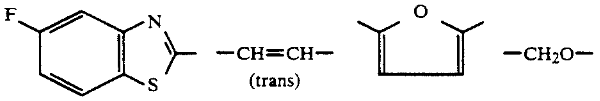 190-193

NMR (300 MHz, $CDCl_3$) 2.48 (s, 3H), 5.10 (s, 2H), 6.54 (m, 2H) delta.

Anal. Calcd. for $C_{27}H_{19}N_4O_2SF.HCl.2H_2O$: C, 58.4; H, 4.4; N, 10.1. Found: C, 58.0; H, 4.3; N, 9.8.

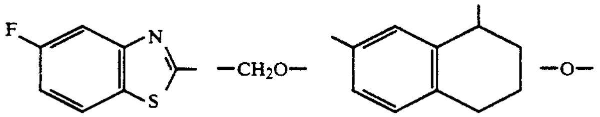 198-200

NMR (300 MHz, $CDCl_3$) 2.54 (s, 3H), 5.44 (s, 2H) delta.

Anal. Calcd. for $C_{31}H_{25}H_4SO_2F$: C, 69.4; H, 4.7; N, 10.4. Found: C, 69.0; H, 4.5; N, 10.3.

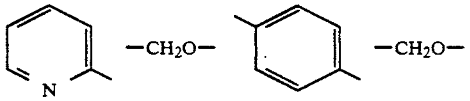 113-115

NMR (300 MHz, $CDCl_3$) 2.49 (s, 3H), 5.11 (s, 2H), 5.22 (s, 2H) delta.

Mass Spec. 422+

Hydrochloride Salt: 235-238.

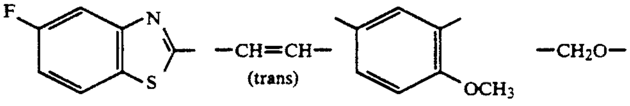 201-203

NMR (300 MHz, $CDCl_3$) 2.51 (s, 3H), 3.93 (s, 3H), 5.20 (s, 2H) delta.

Mass Spec. 522+.

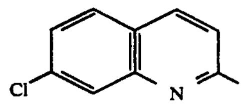 $-CH{=}CH-$ (trans) 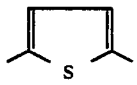 $-CH_2O-$ 167-169

NMR (300 MHz, $CDCl_3$) 2.53 (s, 3H), 5.31 (s, 2H) and 7.84 (AB doublet, 1H, J=16 Hz).

Mass Spec. 508+.

EXAMPLE 14

1-[4-[3-(5-Fluorobenzothiazol-2-ylmethoxy)-phenylethyl]phenyl]-2-methyl-1H-imidazo[4,5-c]-pyridine (Het=5-fluorobenzothiazol-2-yl; A=$-CH_2O-$; W=1,3$-C_6H_4$; and B=$-(CH_2)_2-$)

A. 3-(5-fluorobenzothiazol-2-ylmethoxy)benzyl triphenyl phosphonium bromide

A mixture of 2.01 g of the product of Preparation P and 1.5 g of triphenyl phosphine in 100 ml of toluene were heated to reflux for 20 hours. The reaction mixture was cooled and the solids filtered and dried, 3.0 g.

B. 1-[4-[3-(5-fluorobenzothiazol-2-ylmethoxy)phenylethenyl]phenyl]-2-methyl-1H-imidazo-[4,5-c]pyridine Using the procedure of Preparation E1, 1.55 g of the product of Example 14A, 500 mg of the product of Preparation C and 0.928 ml of 2.5M solution of n-butyl lithium in 40 ml of dry tetrahydrofuran gave, after workup and chromatography, 311 mg of the titled product, m.p. 178°-181° C.

C. 1-[4-[3-(5-fluorobenzothiazol-2-ylmethoxy)-phenylethyl]phenyl]-2-methyl-1H-imidazo-[4,5-c]pyridine A mixture of 200 mg of the product of Example 14C and 100 mg of 5% palladium-on-charcoal in 10 ml of methanol and 10 ml of tetrahydrofuran was shaken in a hydrogen atmosphere at 30 psi for 30 hours. The catalyst was filtered and the filtrate concentrated in vacuo to give 200 mg of an oil. Flash chromatographing on silica gel gave 32 mg of a semi-solid which was recrystallized from ethyl acetate-hexane 14 mg, m.p. 172°-174° C.

The NMR (300 MHz, $CDCl_3$) showed absorption at 2.5 (s, 3H), 2.97 (m, 4H) and 5.44 (s, 2H) delta.

Mass Spec.: Calcd. 494.1577; Found: 494.1570.

EXAMPLE 15

1-[4-[3-(5-Fluorobenzothiazol-2-ylaminocarbonyl)-phenylmethoxy]phenyl]-2-methyl-1H-imidazo-[4,5-c]pyridine (Het=5-fluorobenzothiazol-2-yl; A=$-NHCO-$; W=1,3-$C_6H_4$; and B=$-CH_2O-$)

A. 1-[4-(3-methoxycarbonylphenylmethoxy)phenyl]-2-methyl-1H-imidazo[4,5-c]pyridine Using the procedure of Example 3, 775 mg of methyl 3-hydroxymethylbenzoate, 1.05 g of the product of Preparation A, 122 mg of triphenyl phosphine and 73 μl of diethyl azodicarboxylate in 10 ml of dry tetrahydrofuran gave 886 mg of the desired product as a semi-solid.

B. 1-[4-(3-carboxyphenylmethoxy)phenyl]-2-methyl-1H-imidazo[4,5-c]pyridine

To a stirred solution of 880 mg of the product of Example 15A in 15 ml of methanol was added 5.9 ml of a 1.0N solution of aqueous sodium hydroxide and the resulting reaction mixture heated to reflux for 4 hours. The methanol was removed in vacuo and the residual solution (5 ml) was diluted with 15 ml of water and the pH adjusted with 2N hydrochloric acid to about 7. The resulting precipitate was filtered and dried, 642 mg, m.p. 255°-258° C.

C. 1-[4-[3-(5-fluorobenzothiazol-2-ylaminocarbonyl)-phenylmethoxy]phenyl]-2-methyl-1H-imidazo[4,5-c]-pyridine To a stirred suspension of 300 mg of the product of Example 15B, 147 mg of 2-amino-5-fluorobenzothiazole and 191 mg of 1-hydroxybenzotriazole in 20 ml of dimethylformamide was added 189 mg of dicyclohexylcarbodiimide and the reaction mixture allowed to stand for 3 days. The reaction mixture was diluted with 400 ml of ethyl acetate and washed with water (1×400 ml), 0.5N aqueous sodium hydroxide solution (1×400 ml) and water (1×400 ml). The organic layer was dried and concentrated to give 400 mg of solid which was chromatographed on silica gel with 7.5% methanolmethylene chloride (v:v), 231 mg. A sample was recrystallized from ethyl acetate-hexane, m.p. 244°-246° C.

The NMR (300 MHz, $CDCl_3$) showed absorption at 2.44 (s, 3H) and 5.31 (s, 2H) delta.

Anal. Calcd. for $C_{28}H_{20}N_5O_2SF$: C, 66.0; H, 4.0; N, 13.7. Found: C, 65.9; H, 3.8; N, 13.4.

EXAMPLE 16

4-(2-Methyl-1H-imidazo[4,5-c]pyrid-1-yl)-benzaldehyde, 3-(5-fluorobenzothiazol-2-ylethenyl)phenylglycol acetal (Het=5-fluorobenzothiazol-2-yl; A=(trans)$-CH{=}CH-$; W=1,3 $-C_6H_4$; and B = 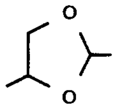

A mixture of 625 mg of 3-(5-fluorobenzothiazol-2-ylethenyl)phenylglycol, 517 mg of 1-(4-formylphenyl)-2-methyl-1H-imidazo[4,5-c]pyridine and 452 mg of 4-toluenesulfonic acid in 60 ml of toluene was refluxed with a Dean-Stark trap for 4 hours. The resulting suspension was cooled, diluted with 400 ml of ethyl acetate and washed with 40 ml of 1N aqueous sodium hydroxide, water (1×40 m) and a brine solution. The organic phase was dried over magnesium sulfate and concentrated to give 1.1 g of crude product which was chromatographed on silica gel (7.5% methanol-92.5% methylene chloride—v:v), 941 mg. The purified material was triturated with hexane (100 ml) to give 857 mg, m.p. 105° C. (dec.).

The NMR (300 mHz, $CDCl_3$) showed absorption at 2.55 (s, 3H), 3.90 (m, 1H), 4.50 (t, 1H), 5.31 (t, 1H) and 6.20 (s, 1H) delta.

EXAMPLE 17

Using the procedure of Example 16, and starting with the appropriate reagents, the following compounds were prepared:

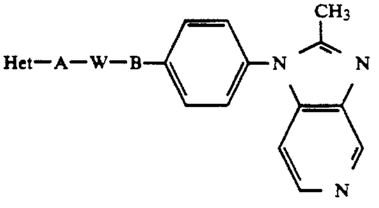

| Het | A | W | B | m.p. °C. |
|---|---|---|---|---|
| 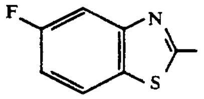 | $-CH_2O-$ | 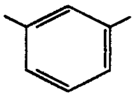 | 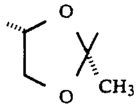 | 186–188 |

Mass Spec. Calcd. for $C_{16}H_{15}NO_3SF$: 552.1632. Found: 552.1675.

| | | | | |
|---|---|---|---|---|
| 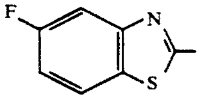 | $-CH_2O-$ | 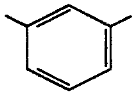 | 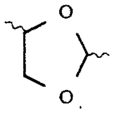 | — |

Mass. Spec. Calcd. for $C_{30}H_{23}N_4O_3SF$: 538.1475. 538.1544.

EXAMPLE 18

1-[4-[3-(5-Fluorobenzothiazol-2-ylcarbamyl)phenylmethoxy]phenyl-2-methyl-1H-imidazo[4,5-c]pyridine (Het=5-fluorobenzothiazol-2-yl; A=—CONH—; W=1,3—$C_6H_4$; and B=—$CH_2O$—)

Using the general coupling procedure of Example 15C, 73 mg of 5-fluorobenzothiazol-2-carboxylic acid, 128 mg of 1-[4-(3-aminophenylmethoxy)phenyl]-2-methyl-1H-imidazo[4,5-c]pyridine, 75 mg of 1-hydroxybenzotriazole and 92 mg of dicyclohexylcarbodiimide in 5 ml of dimethylformamide gave 500 mg of crude product. The semi-solid was chromatographed on silica gel (5% methanol-95% methylene chloride—v:v) to give 131 mg. A small portion was recrystallized from ethyl acetate-hexane, m.p. 222°–224° C.

The NMR (300 MHz, $CDCl_3$) showed absorption at 2.50 (s, 3H) and 5.18 (s, 2H) delta.

Anal. Calcd. for $C_{28}H_{20}N_5SO_2F$: C, 66.0; H, 4.0; N, 13.7. Found: C, 65.5; H, 3.9; N, 13.3.

EXAMPLE 19

N-(Pyrid-2-yl)-2-[4-(2-methylimidazo[4,5-c]-pyrid-1-yl)benzyloxylbenzamide (Het=2-pyridyl; A=—NHCO—; W=1,2-$C_6H_4$; and B=—$OCH_2$—

A. methyl 2-[4-(2-methylimidazo[4,5-c]pyrid-1-yl)benzyloxy]benzoate

4-[2-Methylimidazo[4,5-c]pyrid-1-yl]benzyl alcohol (2.39 g), methyl salycylate (1.67 g) and triphenylphosphine (2.88 g) were dissolved in dry tetrahydrofuran (50 ml). Diethylazodicarboxylate (2.09 g) was added dropwise over 5 minutes. The resulting solution was stirred at room temperature for 1 hour then evaporated to dryness under vacuum. The residue was chromatographed on silica (Merck, Kieselgel 60) eluting with dichloromethane/methanol (97:3 v:v). The product containing fractions were evaporated and the residue crystallized from ether to give 3.5 g of the desired product, m.p. 126°–128° C.

B. 2-[4-(2-methylimidazo[4,5-c]pyrid-1-yl)benzyloxy]benzoic acid

Methyl 2-[4-(2-methylimidazo[4,5-c]pyrid-1-yl)benzyloxylbenzoate (3.73 g) was dissolved in industrial methanol (100 ml) and 2N sodium hydroxide solution (20 ml) was added. The solution was stirred at room temperature for 2 hours then evaporated to low bulk. The concentrated solution was poured into water, washed with dichloromethane (2×50 ml) then acidified with glacial acetic acid. This mixture was reextracted with dichloromethane (3×75 ml). The combined acid extracts were dried over sodium sulfate, filtered, and evaporated to dryness to yield the titled product, 2.03 g, m.p. 217°–219° C.

C. N-(pyrid-2-yl)-2-[4-(2-methylimidazo[4,5-c]pyrid-1-yl) benzyoxybenzamide

2-[4-(2-Methylimidazo[4,5-c]pyrid-1-yl)benzyloxylbenzoic acid (1.44 g) was stirred in dry dichloromethane (50 ml) and three drops of dimethylformamide were added. Oxalyl chloride (1.02 g) was added to dropwise over 5 minutes and the resulting solution stirred at room temperature for 2 hours then evaporated to dryness. The residue was redissolved in dry dichloromethane (20 ml) and cooled in an ice bath. 2-Aminopyridine (1.13 g) was dissolved in dichloromethane (20 ml) and cooled in an ice bath. The cold solution of the acid chloride was then added to the 2-aminopyridine solution over 3 minutes and the reaction mixture stirred for 30 minutes then poured into ethyl acetate (300 ml). The organic solution was washed with water (2×100 ml), dried over sodium sulfate, filtered, and evaporated to dryness. The residue was purified by column chromatography silica (Merck, Kieselgel 60) eluting with dichloromethane/methanol (97:3 v:v). The product containing fractions were evaporated and the residue washed with ether to yield the title amide as a white solid, 760 mg, m.p. 210°-213° C.

Anal. Calcd. for $C_{26}H_{21}N_5O_2.\frac{1}{2}H_2O$: C, 70.3; H, 5.0; N, 15.8 Found: C, 70.2; H, 4.8; N, 15.7.

EXAMPLE 20

Starting with the appropriate reagents and using the procedure of Example 3, the following compounds were prepared:

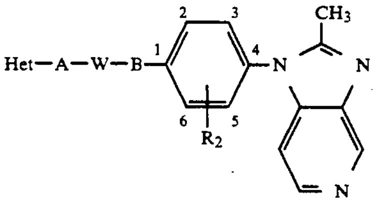

| Het | A | W | B | $R_2$ | m.p. °C. |
|---|---|---|---|---|---|
| 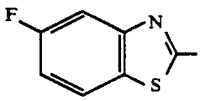 | —CH=CH— (trans) | 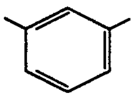 | $-CH_2O-$ | 3-F | 193-194 |

NMR (300 MHz, $CDCl_3$): 2.50 (s, 3H) and 5.18 (s, 2H) delta.

Anal. Calcd. for $C_{29}H_{20}N_4OSF_2$: C, 68.2; H, 4.0; N, 11.0. Found: C, 68.2; H, 3.8; N, 10.9.

| | | | | | |
|---|---|---|---|---|---|
| 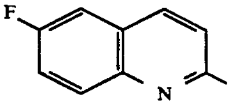 | $-CH_2O-$ | 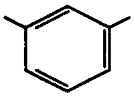 | $-CH_2O-$ | 3-F | 119-121 |

NMR (300 MHz, $CDCl_3$): 2.48 (s, 3H), 5.11 (s, 2H) and 5.38 (s, 2H) delta.

Anal. Calcd. for $C_{30}H_{22}N_4O_2F_2$: C, 68.4; H, 4.6; N, 10.6. Found: C, 68.9; H, 4.5; N, 10.7.

| | | | | | |
|---|---|---|---|---|---|
| 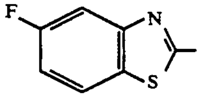 | 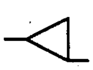 | 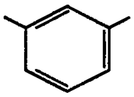 | $-CH_2O-$ | H | 147-148 |

NMR (300 MHz, $CDCl_3$): 2.51 (s, 3H) and 5.13 (s, 2H) delta.

Anal. Calcd. for $C_{30}H_{23}N_4OSF$: C, 71.1; H, 4.6; N, 11.1. Found: C, 71.1; R, 4.4; N, 11.0.

| | | | | | |
|---|---|---|---|---|---|
| 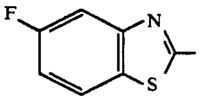 | $-CH_2O-$ | 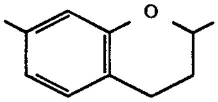 | $-CH_2O-$ | H | 196-198 |

NMR (300 MHz, $CDCl_3$) 2.49 (s, 3H) and 5.44 (s, 2H) delta.

Anal. Calcd. for $C_{31}H_{25}N_4SO_3F$: C, 67.2; H, 4.3; N, 9.9. Found: C, 67.4; H, 4.6; N, 10.1.

| | | | | | |
|---|---|---|---|---|---|
| 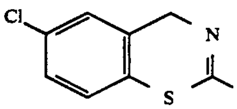 | —C=CH— (trans) | 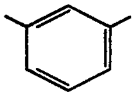 | $-CH_2O-$ | H | 200(dec) |

NMR (300 MHz, $CDCl_3$) 2.58 (s, 3H) and 6.24 (s, 2H) delta.

Anal. Calcd. for $C_{30}H_{23}N_4SOCl$: C, 58.7; H, 4.9; N, 9.1. Found: C, 58.2; H, 5.2; N, 9.5.

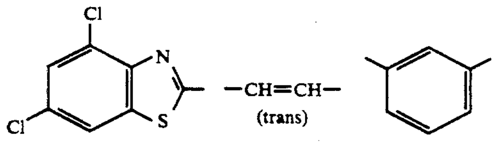
—CH=CH— (trans) —$CH_2O$— H 153-155

NMR (300 MHz, $CDCl_3$) 2.51 (s, 3H) and 5.18 (s, 2H) delta.

Anal. Calcd. for $C_{29}H_{20}N_4SOCl_2$: C, 64.1; H, 3.7; N, 10.3. Found: C, 64.3; H, 3.8; N, 9.5.

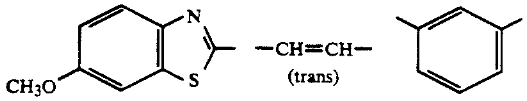
—CH=CH— (trans) —$CH_2O$— H 154-156

NMR (300 MHz, $CDCl_3$) 2.50 (s, 3H), 3.87 (s, 3H) and 5.17 (s, 2H) delta.

Anal. Calcd. for $C_{30}H_{24}N_4SO_2$: C, 71.4; H, 1.8; N, 11.1. Found: C, 71.2; R, 4.9; N, 11.0.

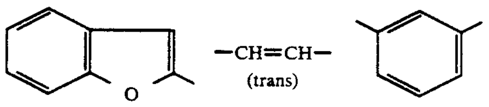
—CH=CH— (trans) —$CH_2O$— H 221-223 (HCl)

NMR (300 MHz, $CDCl_3$) 2.54 (s, 3H) and 5.25 (s, 2H) delta.

Anal. Calcd. for $C_{30}H_{23}N_3O_2.H_2O$: C, 70.4; H, 5.1; N, 8.2. Found: C, 71.2; H, 5.0; N, 8.3.

PREPARATION A

1-(p-Hydroxyphenyl)-2-methyl-1H-imidazo[4,5-c]pyridine

1. 3-nitro-4-(p-hydroxyphenylamino)pyridine

To a stirred mixture of 50.2 g of p-hydroxyaniline and 38.7 g of sodium bicarbonate in 1.5 l of ethanol was added dropwise 73 g of 3-nitro-4-chloropyridine in 2.0 l of ethanol. After stirring overnight at room temperature, the resulting solids were filtered, washed with water (2 l) and dried, 85.4 g.

2. 3-amino-4-(phenylamino)pyridine

A mixture of 42.7 g of the compound of Preparation A1 and 6 g of Raney nickel in 300 ml of ethanol was shaken in a hydrogen atmosphere at an initial pressure of 50 psi at room temperature overnight. The catalyst was filtered and washed with acetic acid until the wash was clear. The filtrate and washings were combined and concentrated in vacuo to give the product as a dark oil.

3. 1-(p-acetoxyphenyl) -2-methyl-1H-imidazo[4,5-c]pyridine

A stirred mixture of 74.3 g of the compound of Preparation A2 in 1.2 l of acetic anhydride was heated at reflux overnight. The solvent was removed in vacuo and the resulting oil dissolved in 1 l of water and the pH adjusted to 2 with 2N hydrochloric acid. The acid solution was extracted with methylene chloride (3×800 ml) and the pH of the aqueous adjusted to 9 with a 5N sodium hydroxide solution. The basic phase was extracted with ethyl acetate (3×500 ml). The aqueous layer was saved and the organic extracts were combined, dried and concentrated to give 31.8 g of a brown solid. The solids were chromatographed on 1.5 kg of silica dioxide using methylene chloride and methylene chloride—ethanol 2, 4 and 6%. The fractions containing the desired material were combined and concentrated in vacuo to give 15.7 g of the titled product as an oil.

The aqueous layer was treated with 4N hydrochloric acid to give a pH of 7. It was extracted with ethyl acetate, and the extracts combined and concentrated to give 41.3 g of 1-(p-hydroxyphenyl)-2-methyl-1H-imidazo[4,5-c]pyridine as a tan solid.

4. 1-(p-hydroxyphenyl)-2-methyl-1H-imidazo[4,5-c]pyridine

To a stirred mixture of 15.7 g of the oil isolated in Preparation A3 in 250 ml of methanol was added 4.7 g of solid sodium hydroxide and 47 ml of water. After stirring two hours at room temperature the reaction mixture is added to 600 ml of a saturated sodium chloride solution, the pH adjusted to 7 with 2N hydrochloric acid and the product extracted with ethyl acetate (3×800 ml) The extracts were combined, dried over sodium sulfate and concentrated in vacuo to give 10.3 g of product as a brown solid. A small sample was recrystallized from methanol-methylene chloride, m.p. 265°-267° C.

PREPARATION B

1-(p-Hydroxymethylphenyl)-2-methyl-1H-imidazo[4,5-c]pyridine

1. 3-nitro-4-(p-hydroxymethylphenylamino)pyridine

In a manner similar to Preparation A1 88.5 g of 3-nitro-4-chloropyridine, 68.7 g of 4-aminobenzyl alcohol and 46.9 g of sodium bicarbonate in 500 ml of ethanol to give 56.3 g of the titled intermediate.

2. 3-amino-4-(p-hydroxymethylphenylamino)pyridine

Using the reduction procedure of Preparation A2, 9.0 g of the product from Preparation B1, 1.8 g of Raney Nickel in 62.5 ml of ethanol and 187.5 ml of tetrahydrofuran gave the titled product which was used without further purification.

3. 1-(P-acetoxymethylphenyl)-2-methyl-1H-imidazo[4,5-c]pyridine

Employing the procedure of Preparation A3, 39.5 g of crude product obtained by the procedure of Preparation B2 in 477 ml of acetic anhydride was heated to reflux overnight. Work-up gave 18.8 g of product, m.p. 135°-137° C.

4. 1-(p-hydroxymethylphenyl) -2-methyl-1H-imidazo[4,5-c]pyridine

As in Preparation A4, 18.8 g of the product of Preparation B3 in 53.4 ml of water and 215 ml of ethanol containing 5.34 g of sodium hydroxide was stirred at room temperature until all solids dissolved. Work-up gave 13.9 g of the titled product, m.p. 154°-157° C.

PREPARATION C 1-(4-Formylphenyl) -2-methyl-1H-imidazo [4,5-c]pyridine

To 20 ml of methylene chloride containing 890 μl of dimethylsulfoxide cooled to −60° C. and maintained under a nitrogen atmosphere was added dropwise 766 μl of oxalyl chloride over a 5 minute period while maintaining the temperature at −60° C. After stirring for 30 minutes at −60° C., 1.50 g of the product of Preparation B in 20 ml of dry methylene chloride was added dropwise over a 20 minute period. The reaction mixture was stirred at −60° C. for 30 minutes and then at −35° C. for 15 minutes. The reaction was again cooled to -60° C. and treated with 4.37 μl of triethylamine dropwise over a 5 minute period. The reaction mixture was then diluted with 75 ml of methylene chloride and washed with a saturated sodium bicarbonate solution (3×100 ml) and a brine solution (1×100), and dried over sodium sulfate. The solvent was removed in vacuo and the 1.49 g residual chromatographed on 150 g of silica using methanol-methylene (5:95—v:v). The fractions containing the product were combined and concentrated to dryness, 1.29 g.

PREPARATION D m-(5-Fluorobenzothiazol-2-ylmethoxy)aniline 1. 1-(5-fluorobenzothiazol-2-ylmethoxy)-3-nitrobenzene A mixture of 5.0 g of 2-chloromethyl-5-fluorobenzothiazole, 3.38 g of m-nitrophenol, 2.58 g of sodium carbonate, 7.92 g of cesium carbonate and 2.44 g of sodium iodide in 150 ml of acetone was heated to reflux overnight. The solids were filtered and washed with acetone, and the filtrate and washings were combined and concentrated to dryness. The residue was taken up in ethyl acetate (150 ml) which was washed with 1N sodium hydroxide solution, water and a brine solution. The organic phase was dried over sodium sulfate and concentrated to give 7.48 g of a tan solid which was chromatographed on 500 g of silica using 4 1 of methylene chloride—hexane (2:1—v:v), 2 1 (9:1—v:v) and 4 1 of methylene chloride alone. The fractions containing the product were combined and concentrated to give 6.33 g of the titled product.

The NMR (300 MHz, $CDCl_3$) showed absorption at 5.54 (2H) delta.

In a similar manner, starting with 2-chloromethyl-5-trifluoromethylbenzothiazole and 3-hydroxy benzyl alcohol and following this procedure, 3-(5-trifluoromethylbenzothiazol-2-ylmethoxy)benzyl alcohol was prepared, m.p. 117°-119° C., 2-chloromethyl-5-fluorobenzothiazole and 2;7-dihydroxynaphthalene gave 2-(5-fluorobenzothiazol-2-ylmethoxy)-7-hydroxynaphthalene, m.p. 218°-220° C., 2-chloromethyl-6-fluoroquinoline and m-resorcinol gave 3-(6-fluorocruinol-2-ylmethoxy)phenol, m.p. 146°-148° C. and 2-chloromethyl-5-fluorobenzothiazol and methyl 3-hydroxymandelate gave methyl 3-(5-fluorobenzothiazol-2-ylmethoxy)-mandelate, m.p. 99°-101° C.

2. m-(5-fluorobenzothiazol-2-ylmethoxy)aniline

To 60 ml of dry ethanol saturated with hydrogen chloride and under a nitrogen atmosphere at 0° C. was added 6.31 g of the product of Preparation D1. To the resulting reaction mixture was added 4.62 g of iron powder in portions and the reaction stirred at room temperature under nitrogen over a period of two days (65 hours).

The reaction was diluted with water (1 1) and the pH adjusted to 8 with 3N sodium hydroxide. The aqueous was extracted with ethyl acetate (3×500 ml), which was washed with water and a brine solution. The organic phase was dried over sodium sulfate and concentrated to give 5.83 g of material. The residue was chromatographed on 400 g of silica using 15% ethyl acetate—methylene chloride. The fractions containing the product were combined and concentrated to give 3.45 g of product.

The NMR ($CDCl_3$, 300 MHz) showed absorption at 5.42 (2H) and 3.70 (b, 2H) delta.

PREPARATION E m-(5-Fluorobenzothiazol-2yl-trans-ethenyl)aniline 1. 1-(5-fluorobenzothiazol-2-yl-trans-ethenyl)-3-nitrobenzene To a suspension of 7.6 g of 5-fluorobenzothiazol-2-ylmethyl triphenyl phosphonium chloride in 100 ml of dry tetrahydrofuran under a nitrogen atmosphere and cooled to −45° C. was added 1.3 ml of a 1.6M solution of n-butyl lithium and the mixture stirred at −45° C. for 10 minutes and at 0° C. for 10–15 minutes. The mixture was then cooled to −45° C. and 2.5 g of m-nitrobenzaldehyde in 25 ml of dry tetrahydrofuran was added over a period of 10 minutes. The reaction mixture was allowed to stir at −45° C. for one hour and was then allowed to warm to 0° C.

The reaction mixture was concentrated in vacuo and the residue partitioned between water (500 ml) and ethyl acetate (2×500 ml). The organic phase was washed with water and a brine solution and dried over sodium sulfate. Removal of the solvent gave 3.0 g of crude product which was purified by recrystallization from ethyl acetate—hexane, 2.1 g, m.p. 180°-182° C.

In a similar manner was prepared 4-(5-fluorobenzothiazol-2-yl-trans-ethenanol (NMR—300 MHz, $CDCl_3$—1.4 (m, 4H), 2.3 (m, 2H) and 3.65 (m, 2H) by reacting tri-phenyl 5-fluorobenzothiazol-2-ylmethyl phosphonium chloride and 2-hydroxytetrahydropyran, 2-hydroxymethyl-5-(5-fluorobenzothiazol-2-yl-transethenyl)furan m.p. 137°-140° C., by reacting triphenyl 5-fluorobenzothiazol-2-ylmethyl phosphonium chloride and 5-hydroxymethylfurfural and methyl 2-methoxy 5-(5-fluorobenzothiazol-2-yl-trans-ethenyl)benzoate, m.p. 138°-140° C., by reacting triphenyl 5-fluorobenzothiazol-2-methyl phosphonium chloride and methyl 2-methoxy-5-formylbenzoate.

2. m-(5-fluorobenzothiazol-2-yl-trans-ethenyl)aniline

Following the procedure of Preparation D2, 1.78 g of the product of Preparation E1, 1.32 g of iron powder and 50 ml of ethanol saturated with hydrogen chloride gave 1.27 g of the titled product.

PREPARATION F 3-(Quinol-2-ylmethoxy)benzyl alcohol

A mixture of 1.0 g of 2-chloromethylquinoline, 700 mg of 3-hydroxybenzyl alcohol and 2.33 g of potassium carbonate in 20 ml of dry dimethylformamide was stirred at room temperature overnight. The mixture was poured into 600 ml of water and extracted with ethyl acetate (3×200 ml). The extracts were combined, washed with water, 1N sodium hydroxide solution and brine, dried over sodium sulfate and concentrated in vacuo, 1.38 g. The residual oil was chromatographed on 100 g of silica using 800 ml of 2% methanol-methylene chloride (v:v) and 1 l of 4% methanol-methylene chloride (v:v). The fractions containing the titled product were combined and concentrated to give 1.02 g of product.

In a similar manner 4-(5-fluorobenzothiazol-2-ylmethoxy)-4'-hydroxydiphenyl, m.p. 210°-211° C. was prepared from 2-chloromethyl-5-fluorobenzothiazole and 4,4-dihydroxydiphenyl, 3-(5-fluorobenzothiazol-2-ylmethylthio)benzyl alcohol was prepared from 3-mercaptobenzyl alcohol and 2-chloromethyl-5-fluorobenzothiazole and 2-ethoxycarbonyl-7-(5-fluorobenzothiazol-2-ylmethoxy)chroman, m.p. 109°-112° C. was prepared from 2-chloromethyl-5-fluorobenzothiazole and 2-ethoxycarbonyl-7-hydroxychroman.

PREPARATION G

4-Hydroxy-6-(5-fluorobenzothiazol-2-ylmethoxy)chroman 1. 6-hydroxy chroman-4-one A mixture of 36 g of 6-methoxychroman-4-one and 290 ml of 48% hydrogen bromide solution in 290 ml of glacial acetic acid was heated to reflux for 3 hours. The solvent was removed in vacuo and the residue diluted with 2 l of water and stored in a refrigerator overnight. The resulting solid was filtered, washed with water and dried, 25.7 g. The original filtrate was extracted with ethyl acetate and the organic layer dried over sodium sulfate and concentrated to give an additional 4.75 g of the titled product.

2. 6-(5-fluorobenzothiazol-2-ylmethoxy)chroman-4-one

Starting with 2.7 g of 2-chloromethyl-5-fluorobenzothiazol, 2.0 g of the product of Preparation G1 and 5.0 g of potassium carbonate in 80 ml of dry dimethylformamide and following the procedure of Preparation F, gave 1.17 g of the desired product.

3. 4-hydroxy-6-(5-fluorobenzothiazol-2-ylmethoxy) chroman

To a mixture of 1.88 g of the product of Preparation G2 in 75 ml of methanol and 75 ml of tetrahydrofuran cooled to 0°-5° C. under nitrogen was added 216 mg of sodium borohydride in two portions. The cooling bath was removed and the reaction mixture stirred at room temperature for 25 minutes. An additional 75 ml of tetrahydrofuran was added and the mixture heated to 30° C. for 10 minutes. Additional borohydride (216 mg) was added and the reaction continued for 10 minutes. Acetone (5 ml) was added and the solvents removed in vacuo. The residue was partitioned between water and ethyl acetate. The organic layer was separated, washed with water and a brine solution and dried over sodium sulfate. Removal of the solvent gave 1.64 g of the product, which was recrystallized from diisopropyl ether—methylene 849 mg, m.p. 137°-138° C.

PREPARATION H 3-(5-Fluorobenzothiazol-2-yl-trans-ethenyl)benzyl alcohol 1. methyl 3-(5-fluorobenzothiazol-2-yl-transethenyl)benzoate Using the procedure of Preparation El and starting with 5.65 g of 5-fluorobenzothiazol-2-ylmethyl triphenyl phosphonium chloride (prepared by reacting 4.0 g of 2-chloromethyl-5-fluorobenzothiazole and 5.22 g of triphenylphosphine in 50 ml of toluene at reflux temperature for 17 hours), 7.61 ml of 1.6M n-butyl lithium solution in hexane and 2.0 g of methyl 3-formylbenzoate in 80 ml of dry tetrahydrofuran there was obtained 2.92 g of the titled product, m.p. 172°-173° C.

In a similar manner triphenyl 5-chlorobenzothiazol-2-ylmethyl phosphonium chloride was reacted with methyl 3-formylbenzoate to give methyl 3-(5-chlorobenzothiazol-2-yl-trans-ethenyl)benzoate, m.p. 168°-169° C., triphenyl 5-fluorobenzothiazol-2-ylmethyl phosphonium chloride was reacted with ethyl 3-formylcyclohexylcarboxylate to give ethyl 3-(5-fluorobenzothiazol-2-yl-trans-ethenyl) cyclohexylcarboxylate, m.p. 67°-70° C., triphenyl 5-fluorobenzothiazol-2-ylmethyl phosphonium chloride was reacted with methyl 2-formylbenzoate to give methyl 2-(5-fluorobenzothiazol-2-yl-trans-ethenyl)benzoate, m.p. 119°-120° C. and triphenylbenzofur-2-ylmethylphosphonium bromide was reacted with methyl 3-formyl benzoate to give methyl 3-(benzofur-2-yl-trans-ethenyl)benzoate, m.p. 98°-100° C.

2. 3-(5-fluorobenzothiazol-2-yl-trans-ethenyl)benzyl alcohol

To a stirred solution of 200 mg of the product of Preparation H1 in 15 ml of dry tetrahydrofuran at −78° C. was added dropwise 1.3 μl of a 1.0M solution of diisobutylaluminum hydride in tetrahydrofuran and the resulting reaction mixture allowed to stir at −78° C. for one hour. The reaction was slowly allowed to warm to 0° C. over a two hour period and was quenched with 3 ml of ethyl acetate. The reaction was added to 100 ml of 5% aqueous sulfuric acid and extracted with ethyl acetate (2×100 ml). The combined extracts were washed with water (2×20 ml) and a brine solution (2×20 ml), dried over magnesium sulfate and concentrated to give 200 mg of product. Chromatography on silica gel using 2% ethyl acetate—98% methylene chloride (v:v) gave 157 mg of pure product, m.p. 129°-130° C.

An alternate procedure for preparing this benzyl alcohol comprises condensing isophthalaldehyde with 2-methyl-5-fluorobenzothiazole in the presence of acetic anhydride and zinc chloride in hot xylene followed by the reduction of the 3-(5-fluorobenzothiazol-2-yl-trans-ethenyl)benzaldehyde product with sodium borohydride to provide the appropriate benzyl alcohol.

In a similar manner ethyl 3-(5-fluorobenzothiazol-2-yl-trans-ethenyl)cyclohexylcarboxylate was reduced to 1-hydroxymethyl-3-(5-fluorobenzothiazol-2-yl-transethenyl)cyclohexane, m.p. 95°-97° C.

In a similar manner were prepared 2-(5-fluorobenzothiazol-2-yl-trans-ethenyl)benzyl alcohol, m.p. 116°-117° C., 2-hydroxymethyl-7-(5-fluorobenzothiazol-2-yl-methoxy)chroman, m.p. 152 °-154° C., .4-(5-fluorobenzothiazol-2-yl-trans-ethenyl)benzyl alcohol, m.p. 166°-168° C., 3-(benzofur-2-yl-trans-ethenyl)-benzyl alcohol, m.p. 104°-106° C., 3-(5-chlorobenzothiazol-2-yl-transethenyl)benzyl alcohol and 2-methoxy-5(5-fluorobenzothiazol-2-yl-trans-ethenyl)-benzyl alcohol, m.p. 187°-189° C.

PREPARATION I

3-(Quinol-2-yl-trans-ethyl)benzyl alcohol 1. 3-(quinol-2-yl-trans-ethenyl) benzaldehyde A solution of 10.0 ml of 2-methylquinoline 20.9 ml of acetic anhydride and 9.91 g of isophthalaldehyde in 200 ml of xylene was heated to reflux under nitrogen for 7 hours. The cooled reaction was diluted with 1 l of ethyl acetate and the resulting solution was washed with a 10% sodium bicarbonate solution (3×250 ml) and a brine solution, and dried over sodium sulfate. The organic layer was concentrated in vacuo to give 21.7 g of a yellow solid. The residue was chromatographed on 1 kg of silica using 8 l of methylene chloride, 4 l of 3% ethyl acetate—methylene chloride (v:v) and 8 l of 5% ethyl acetate—methylene chloride (v:v). The fractions containing the product were combined and concentrated to give 8.27 g of the titled product.

In a similar manner isophthalaldehyde was reacted with 41-methyl-7-chloroquinoline to give 3-(7-chloroquinol-2-ylethenyl)benzaldehyde, m.p. 148°-150° C., with 1,2-dimethylbenzimidazole to give 3-(1-methylbenzimidazol-2-ylethenyl)benzaldehyde, m.p. 118°-120° C., with 2-methyl-5-chlorobenzoxazole to give 3-(5-chlorobenzoxazol-2-ylethenyl)benzaldehyde, m.p. 140°-142° C., with 2-methyl-4,6-dichlorobenzothiazole to give 3-(4,6-dichlorobenzothiazol-2-ylethenyl) benzaldehyde, m.p. 211°-213° C.

2. 3-(2-quinol-2-1-trans-ethenyl)benzyl alcohol

Starting with 560 mg of the product of Preparation I1 and 82 mg of sodium borohydride in 30 ml of methanol and 10 ml of tetrahydrofuran and using the procedure of Preparation G3 gave 461 mg of the titled product as a white solid.

In a similar manner were prepared 3-(5-chlorobenzoxazol-2-ylethenyl)benzyl alcohol, m.p. 114°-116° C., 3-(1-methylbenzimidazol-2-ylethenyl)benzyl alcohol, m.p. 172°-174° C., 3-(7-chloroquinol-2-ylethenyl)benzyl alcohol, m.p. 138°-140° C. and 3-(4,6-dichlorobenzothiazol-2-ylethenyl)benzyl alcohol, m.p. 177°-179° C.

3. 3-(2-cruinol-2-ylethyl)benzyl alcohol

A mixture of 315 mg of the product of Preparation I2 and 100 mg of 10% palladium-on-charcoal in 25 ml of methanol was shaken in a hydrogen atmosphere at a pressure of 20 psi at room temperature for 80 minutes. The catalyst was filtered and the filtrate concentrated to give 340 mg of a yellow oil. The residue was chromatographed on 30 g of silica using 25% ethyl acetate—methylene chloride (v:v) . The fractions containing the product were combined and concentrated to give 314 mg of a yellow oil which crystallized.

In a similar manner 3-(7-chloroquinol-2-yl-ethenyl)-benzyl alcohol was reduced to 3-(7-chloroquinol-2-ylethyl)benzyl alcohol, m.p. 115°-116° C.

PREPARATION J

3-(7-Chloroquinol-2-yl-trans-ethenyl)benzyl alcohol 1. 3-(7-chloroquinol-2-yl-trans-ethenyl)benzaldehyde Starting with 6.56 g of 2-methyl-7-chloroquinoline, 10.4 ml of acetic anhydride and 4.95 g of isophthalaldehyde in 100 ml of xylene and using the procedure of Preparation I1, there was obtained 5.64 g of the desired product as a yellow solid.

2. 3-(7-chloroquinol-2-yl-trans-ethenyl)benzyl alcohol

Using the procedure of Preparation I2 and starting with 5.6 g of the product of Preparation J1 and 720 mg of sodium borohydride in 300 ml of methanol and 100 ml of tetrahydrofuran there was obtained 3.93 g of the titled product, m.p. 138°-140° C.

PREPARATION K

2-(5-Fluorobenzothiazol-2-yl-trans-ethenyl)6-hydroxymethylpyridine 1. 2-hydroxymethyl-pyridine-6-carboxaldehyde To a cooled (0° C.) solution of 2.0 g of 2,6-pyridineaicarboxaldehyde in 50 ml of methanol was added 240 mg of sodium borohydride and the mixture stirred for 10 minutes. The mixture was allowed to warm to room temperature and was allowed to stir for 15 minutes. A few drops of acetone were added and the methanol removed in vacuo. The residue was dissolved in 200 ml of methylene chloride and the organic solution washed with water (1×250 ml) and a brine solution (1×250 ml) and dried over sodium sulfate. The solvent was removed in vacuo and the residue chromatographed on silica gel to give 324 mg of the desired product as a yellow oil.

2. 2-(5-fluorobenzothiazol-2-yl-trans-ethenyl)-6-hydroxymethylpyridine

A suspension of 1.35 g of 5-fluorobenzothiazol-2-ylmethyl triphenylphosphonium chloride in 8 ml of dry tetrahydrofuran cooled to −40° C. and under a nitrogen atmosphere was added 1.82 ml of a 1.6M solution of n-butyl lithium in hexane dropwise. After stirring for 10 minutes the temperature was raised to 0° C. for 10-15 minutes. The mixture was then cooled to −40° C. again and 200 mg of the product of Preparation K1 was added in 10 ml of dry tetrahydrofuran. The reaction was stirred for one hour and then allowed to warm to room temperature overnight. The reaction mixture was is concentrated in vacuo and the residue partitioned between 300 ml of water and ethyl acetate (2×300 ml). The organic extracts were combined, washed with water and a brine solution and dried over sodium sulfate. The solvent was removed in vacuo and the residue chromatographed on silica gel using 2.5% methanol—97.5% methylene chloride (v:v). The fractions containing the product were combined and concentrated under vacuum, 290 mg, m.p. 179°-181° C.

PREPARATION L

3-(6-fluorobenzothiazol-2-ylmethoxy)benzyl alcohol

A mixture of 215.5 mg of 3-hydroxybenzyl alcohol, 350 mg of 2-chloromethyl-6-fluorobenzothiazole and 590 mg of potassium carbonate in 8 ml of dimethylformamide was stirred overnight under a nitrogen atmosphere at room temperature. The reaction mixture was poured into water and extracted with ethyl acetate. The organic phase was separated, washed with a 1N aqueous sodium hydroxide solution, water and a brine solution and dried over sodium sulfate. Removal of the solvent gave 440 mg of a solid which was chromatographed on 50 g of silica gel using 20% ethyl acetate—80% methylene chloride (v:v) to give 373 mg of product, m.p. 99°-100° C.

By a similar procedure 3-(5,6-difluorobenzothiazol-2-ylmethyloxy)benzyl alcohol, m.p. 98°-100° C., 3-(5-fluorobenzothiazol-2-ylmethoxy)benzyl alcohol, m.p. 139°-140° C., 3-(7-chloroquinol-2-ylmethoxy)benzyl alcohol, m.p. 128°-129° C., and 3-(2-pyridylmethoxy)-benzyl alcohol, NMR (300 MHz, $CDCl_3$) 5.10 (s, 2H) were prepared.

PREPARATION M alpha-methyl 3-(6-fluorocruinol-2-ylmethoxy)benzyl alcohol

1. 3-(6-fluoroquinol-2-ylmethoxy)acetophenone

Using the procedure of Preparation L, 3.65 g of 3-hydroxyacetophenone, 5.0 g of 2-chloromethyl-6-fluoroquinoline and 8.6 g of potassium carbonate in 100 ml of dimethylformamide gave, after chromatographing on 500 a of silica gel, 1.76 g of the titled product, m.p. 79°-80° C.

2. alpha methyl 3-(6-fluoroquinol-2-ylmethoxy)benzyl alcohol

To a solution of 770 mg of the compound of Preparation MI in 35 ml of methanol and 20 ml of tetrahydrofuran was added 99 mg of sodium borohydride all at once. After stirring at room temperature the reaction mixture was concentrated and the residue partitioned between water and ethyl acetate. The organic phase was separated, washed with water and a brine solution and dried over sodium sulfate. Concentration gave 800 mg of product which was purified by chromatographing on 85 of silica gel using from 15% ethyl acetate—85% methylene chloride (v:v) to 20%-80% of the same solvents, 768 mg, m.p. 60°-62° C.

In a similar manner was prepared alpha methyl 3-(5-fluorobenzothiazol-2-ylmethoxy)benzyl alcohol, m.p. 75°-90° C.

PREPARATION N

3-(5-fluorobenzothiazol-2-ylmethoxy)phenylisopropanol

To a solution of 920 mg of 3-(5-fluorobenzothiazol-2-ylmethoxy)acetophenone, m.p. 124°-125° C., prepared by the procedure of Preparation M1, in 25 ml of dry tetrahydrofuran cooled to 0° C. was added 3.05 ml of a 1.5M solution of methyl magnesium bromide in toluene—tetrahydrofuran over a period of 5 minutes. After stirring the reaction for 30 minutes the reaction mixture was poured into water (500 ml), the pH adjusted to 5 and the product extracted with ethyl acetate. The organic phase was washed with water and a brine solution and dried over sodium sulfate. Removal of the solvent gave 1.0 g of product which was purified by chromatographing on silica gel to give 438 mg of a yellow oil.

PREPARATION O

4-Hydroxy-6-(7-chloroquinol-2-ylmethoxy)chroman

1. 6-(7-chloroquinol-2-ylmethoxy)chroman-4-one

Starting with 1.04 g of 2-chloromethyl-7-chloroquinoline, 808 mg of the product of Preparation G1 and 1.7 g of potassium carbonate in 20 ml of dimethylformamide and using the procedure of Preparation F gave 1.22 g of the titled product, m.p. 163°-164° C.

2. 4-hydroxy-6-(7-chloroquinol-2-ylmethoxy)chroman

Using the procedure of Preparation G3 and starting with 1.01 g of the product of Preparation O1 and 125 mg of sodium borohydride in 40 ml of methanol and 40 ml of tetrahydrofuran gave 1.0 g of product, m.p. 139°-140° C.

In a similar manner was prepared 4-hydroxy-6-(6-fluoroquinol-2-ylmethoxy)chroman, m.p. 141°-142° C., 1-hydroxy-7-(5-fluorobenzothiazol-2-ylmeth naphthalene, m.p. 120°-122° C. and 4-hydroxy-6-(2-guinol-2-ylmethoxy)chroman, m.p. 135°-137° C.

PREPARATION P

3-(5-Fluorobenzothiazol-2-ylmethoxy)benzyl bromide

To a solution of 1.04 g of 3-(5-fluorobenzothiazol-2-ylmethoxy)benzyl alcohol (Preparation L) in 60 ml of dry tetrahydrofuran was added 2.38 g of carbontetrabromide and 1.89 g of triphenylphosphine and the reaction stirred under nitrogen at room temperature for 1.5 hours. The reaction mixture was filtered, treated with 100 ml of water and extracted with ethyl acetate. The extracts were washed with water and a brine solution and dried over sodium sulfate. The solvent was removed and the residual brown solid chromatographed on 200 g of silica gel using from 5-10% ethyl acetate—95-90% hexane (v:v). The fractions containing the product were combined and concentrated to give 910 mg of the titled product, m.p. 99°-100° C.

In a similar manner, 3-(5-fluorobenzothiazol-2-ylmethylthio)benzyl alcohol was converted to 3-(5-fluorobenzothiazol-2-ylmethylthio)benzyl bromide, m.p. 163°-165° C.

PREPARATION Q

(+) cis-3-(3-Methoxycarbonylbenzyl)-4-hydroxy-6-(5-fluorobenzothiazol-2-ylmethoxy)chroman To a cold (0° C.) solution of 500 mg of (+)-cis-3-(3-carboxybenzyl)-4-hydroxy-6-(5-fluorobenzothiazol-2-ylmethoxy)chroman (EPO Application 313295-A; published Oct. 17, 1988) in 10 ml of diethyl ether and 30 ml of tetrahydrofuran was added an excess of diazomethane and the reaction stirred at 0° C. for 2 hours. The reaction was allowed to warm to room temperature and 0.5 ml of acetic acid was added followed after 30 minutes by 100 ml of water and 100 ml of diethyl ether. The organic phase was washed with a brine solution, dried over sodium sulfate and concentrated to give 550 mg of a foam.

PREPARATION R

3-(Phenylethenyl)benzyl alcohol

1. methyl 3-(phenyl-trans-ethenyl)benzoate

Using the procedure of Preparation H1, 2.37 g of triphenyl benzyl phosphonium chloride (Aldrich), 1.0 g of methyl 3-carbonylbenzoate and 2.44 ml of 2.5M solution of n-butyl lithium in hexane in 50 ml (total) of tetrahydrofuran gave 208 mg of the titled product, m.p. 108°-109° C.

2. 3-(Phenyl-trans-ethenyl)benzyl alcohol

Employing the procedure of Preparation H2, 186 mg of the product of Preparation R1 and 1.64 μl of a 1M solution of diisobutylaluminum hydride in tetrahydrofuran dissolved in 15 ml of dry tetrahydrofuran at −78° C. for one hour and 0° C. for 2-3 hours gave on work-up 107 mg of the titled product, m.p. 91°-92° C.

PREPARATION S 3-(7-Chloroquinol-2-yl-trans-ethenyl)-alpha-methylbenzyl alcohol

To a solution of 1.0 g of the product of Preparation il in 20 ml of dry tetrahydrofuran cooled to 0° C. was added 2.61 ml of a 1.5M solution of methyl magnesium bromide in tetrahydrofuran. After 30 minutes a few drops of water was added to the reaction mixture and the solvent removed in vacuo. The residue was treated with 100 ml of water and 100 ml of methylene chloride. The organic layer was washed with a brine solution, dried over sodium sulfate and concentrated in vacuo. The residue was chromatographed on silica using methylene chloride—ethyl acetate (85:5; v:v) to give 980 mg of the product as a pale yellow solid.

In a similar manner 3-(5-fluorobenzothiazol-2-yl-trans-ethenyl) 1 alcohol m.p. 114°-116° C. was prepared by the reaction of methyl magnesium bromide and 3-(5-fluorobenzothiazol-2-yl-trans-ethenyl)benzaldehyde (Preparation T).

PREPARATION T 3-(5-Fluorobenzothiazol-2-yl-trans-ethenyl)benzaldehyde

To a solution of 1.5 g of 3-(5-fluorobenzothiazol-2-yl-trans-ethenyl)benzyl alcohol (Preparation H2) in 40 ml of methylene chloride and 25 ml of dimethylsulfoxide at −60° C. was added a solution of 0.64 ml of oxalyl chloride in 20 ml of dry methylene chloride containing 0.74 ml of dimethylsulfoxide. After stirring at −60° C. for 35 minutes the reaction mixture was allowed to warm to −35° C. for 25 minutes. The mixture was again cooled to −60° C. and 3.65 ml of triethylamine was added over a period of 5 minutes. The mixture was allowed to warm to room temperature and was treated with 200 ml of water. The organic phase was washed with a brine solution, dried over sodium sulfate and concentrated in vacuo to give after trituration with ethyl acetate—hexane 1.2 g. A sample was recrystallized from ethyl acetate—hexane, m.p. 151°-152° C.

PREPARATION U 3-(6-Fluoroquinol-2-yl-trans-ethenyl)-alpha-methylbenzyl alcohol 1. 3-(6-fluoroquinol-2-yl-trans-ethenyl)benzaldehyde Using the procedure of Preparation I1, 5.04 g of 2-methyl-6-fluoroquinoline, 4.20 g of isophthaldehyde and 8.86 ml of acetic anhydride in 100 ml of xylene gave 4.40 g of the titled product as a pale yellow solid, m.p. 110°-111° C.

2. 3-(6-fluoroquinol-2-yl-trans-ethenyl)-alpha-methylbenzyl alcohol

Employing the procedure of Preparation S, 500 mg of the product of Preparation T1 and 1.32 ml of a 1.5M solution of methyl magnesium bromide in tetrahydrofuran in 10 ml of tetrahydrofuran gave 430 mg of product, m.p. 107°-109° C.

PREPARATION V 3-(Pyrid-2-yl-trans-ethenyl)benzyl alcohol 1. methyl 3-(pyrid-2-yl-trans-ethenyl)benzoate Using the procedure of Preparation H1, 750 mg of methyl 3-formylbenzoate, 2.14 g of triphenyl 2-pyridylmethyl phosphonium chloride and 2.0 ml of a 2.5M solution of n-butyl lithium in 30 ml of dry tetrahydrofuran gave 496 mg of the titled product.

2. 3-(pyrid-2-yl-trans-ethenyl)benzyl alcohol

Employing the procedure of Preparation R2, 409 mg of the product of Preparation V1 and 4.5 μl of a 1M solution of diisobutylaluminum hydride in tetrahydrofuran in 15 ml of dry tetrahydrofuran gave 351 mg of the titled product.

PREPARATION W 3-(5-Fluorobenzothiazol-2-ylethyl)benzyl alcohol 1. methyl 3-(5-fluorobenzothiazol-2-ylethyl)benzoate A mixture of 700 mg of the product of Preparation H1 and 210 mg of 10% palladium-on-charcoal in 30 ml of methanol was shaken in a hydrogen atmosphere at 40 psi for 4 hours. The catalyst was filtered and the filtrate concentrated in vacuo. The residue was flash chromatographed on silica (80% methylene chloride—20% methanol—v:v) to give 359 mg of titled product.

2. 3-(5-fluorobenzothiazol-2-ylethyl)benzyl alcohol

The product of Preparation W1 (350 mg) was reacted with 1.1 ml of a 1.0M solution of lithium aluminum hydride in 10 ml of dry tetrahydrofuran by the procedure of Preparation H2 to give on work-up 208 mg of product as a yellow solid.

PREPARATION X 3-(5-Fluorobenzothiazol-2-ylaminomethyl)benzyl alcohol

A mixture of 1.38 g of 3-hydroxymethylbenzaldehyde, 1.7 g of 2-amino-5-fluorobenzothiazole and 200 mg of p-toluene sulfonic acid in 100 ml of toluene were refluxed with a Dean-Stark trap for 18 hours. The reaction mixture was concentrated in vacuo and the residue dissolved in 50 ml of dry tetrahydrofuran and 50 ml of methanol and cooled to 0° C. To the resulting solution was added 945 mg of sodium borohydride over a period of 20 minutes. The reaction mixture was stirred at 0° C. for 2 hours, was hydrolyzed by the addition of an ammonium chloride solution and was concentrated to a small volume in vacuo. The residual suspension was added to 200 ml of water, the pH adjusted to 10 and the resulting mixture extracted with ethyl acetate (2×200 ml). The extracts were combined, washed with water and a brine solution and dried over magnesium sulfate. Removal in vacuo of the solvent gave 2 g of material which was chromatographed on silica gel to give 235 mg of pure product.

The NMR (300 MHz, $CDCl_3$) showed absorption at 4.45 (s, 2H) and 4.55 (s, 2H)

PREPARATION Y

3-(5-Fluorobenzothiazol-2-yl-trans-ethenyl)phenylglycol

1. methyl 3-vinylbenzoate

To a stirred suspension of 590 mg of methyl triphenylphosphonium iodide in 50 ml of dry tetrahydrofuran cooled to −50° C. was added dropwise 5.3 ml of 2.5M n-butyl lithium in hexane. The resulting mixture was allowed to warm to 0° C. over a period of one hour. The mixture was then cooled to −70° C. and 2.0 g of methyl 3-formylbenzoate in 20 ml of dry tetrahydrofuran was added dropwise over a period of 20 minutes. The reaction mixture was allowed to warm to room temperature and stir overnight. The reaction mixture was concentrated in vacuo and the residue treated with water (200 ml) and extracted with diethyl ether (2×200 ml). The extracts were combined, washed with water and a brine solution and dried over magnesium sulfate. Removal of the solvent gave 2 g of an oil which was flash chromatographed on silica gel (30% ethyl acetate—hexane; v:v) , 2.0 g. Distillation in vacuo gave 1.36 g.

2. 3-methoxycarbonylphenylglycol

Starting with 1.3 g of the product of Preparation Y1 and using the procedure of J. Am. Chem. Soc. 110, 3937 (1988) there was obtained 920 mg of the titled product as an oil.

3. acetone 3-methoxycarbonylphenylglycol ketal

A mixture of 900 mg of the product of Preparation Y2 and 5-10 mg of 4-toluenesulfonic acid in 20 ml of 2,2-dimethoxypropane was allowed to stand for 2 days. The mixture was concentrated and the residue treated with 300 ml of diethyl ether. The ether solution was washed with 300 ml of a saturated sodium bicarbonate solution, water (300 ml) and a brine solution (300 ml). to The organic phase was dried and concentrated to an oil, 1.0 g which was flash chromatographed on silica (35% ethyl acetate—hexane; v:v) to give 940 mg of product.

4. acetone 3-hydroxymethylphenylglycol ketal

Using the procedure of Preparation H2, 936 mg of the product of Preparation Y3 and 9.9 ml of a 1.0M solution of diisobutyl aluminum hydride (tetrahydrofuran) in 20 ml of dry tetrahydrofuran gave 820 mg of the titled product as an oil.

5. acetone 3-formylphenylglycol ketal

Employing the procedure of Preparation S 800 mg of the product of preparation Y4, 545 μl (600 mg) of dimethylsulfoxide, 469 μl (682 mg) of oxalyl chloride and 2.88 ml (1.74 g) of triethyl amine in 20 ml of methyl chloride gave 671 mg of the desired product as an oil.

6. acetone 3-(5-fluorobenzothiazol-2-yl-transethenyl)phenylglycol ketal

Following the procedure of Preparation E1, 665 mg of the product of Preparation Y5, 1.87 g of 5-fluorobenzothiazol-2-yl triphenyl phosphonium chloride and 15 μl of 2.5M n-butyl lithium solution (hexane) in 20 ml of dry tetrahydrofuran gave, on work-up, 942 mg of product, m.p. 74°-77° C.

7. 3-(5-fluorobenzothiazol-2-yl-trans-ethenyl)phenylglycol

A suspension of 925 mg of the product of Preparation Y6 in 10 ml of tetrahydrofuran was treated with 5 ml of 2N hydrochloric acid and allowed to stand for 30 hours. The reaction mixture was diluted with water (200 ml) and the product extracted with ethyl acetate (2×200 ml). The extracts were combined, washed with a saturated sodium bicarbonate solution, water (1×40 ml) and a brine solution. The organic phase was dried over magnesium sulfate and concentrated to give 1 g of solid which was recrystallized from ethyl acetate—hexane, 660 mg, m.p. 126°-128° C.

Mass Spec. 315+

PREPARATION Z

4-Hydroxy-6-(5-fluorobenzothiazol-2-yl-trans-ethenyl)-chroman

1. 6-methylchroman-4-one glycol ketal

A mixture of 7.2 g of 6-methylchroman-4-one, 4.13 g of glycol and 360 mg of 4-toluenesulfonic acid in 200 ml of benzene was refluxed with a Dean-Stark trap for 18 hours. The mixture was diluted with diethyl ether (200 ml) and washed with a saturated sodium bicarbonate solution (2×400 ml), water (1×400 ml) and a brine solution (1×400 ml). The organic phase was dried over magnesium sulfate and concentrated to give an oil. The residue was flash chromatographed on silica (30% ethyl acetate—hexane; v:v) to give 7.2 g of product.

2. 6-bromomethylchroman-4-one glycol ketal

A mixture of 7.2 g of the product of Preparation Z1, 6.2 g of N-bromosuccinimide and 720 mg of benzoylperoxide in 200 ml of carbontetrachloride was heated to reflux for 4 hours. The solvent was removed in vacuo and the residue treated with 400 ml of diethyl ether. The solution was washed with a saturated sodium bicarbonate solution (1×400 ml), water (1×400 ml) and a brine solution (1×400 ml) and the organic phase dried over magnesium sulfate. Removal of the solvent gave 6 g of an oil which was flash chromatographed on silica (30% ethyl acetate—hexane; v:v) to give 2.3 g of the titled product as an oil.

3. 6-formylchroman-4-one glycol ketal

A mixture of 2.3 g of the product of Preparation Z2 and 11.3 g of bis(tetra-n-butylammonium)dichromate in 100 ml of chloroform was refluxed for 2 hours. The mixture was cooled to 0° C., diluted with 100 ml of diethyl ether and treated with 10 g of silica gel. The mixture was filtered and the solids washed with 400 ml of diethyl ether. The filtrates were combined and concentrated to give 2 g of an oil. The residue was flash chromatographed on silica (50% ethyl acetate—hexane; v:v) to give 630 mg of the title product as a yellow solid, m.p. 70°-73° C.

4. 6-(5-fluorobenzothiazol-2-yl-trans-ethenyl)chroman-4-one glycol ketal

Using the procedure of Preparation E1 and starting with 1.68 g of 5-fluorobenzothiazol-2-ylmethyl triphenylphosphonium chloride, 650 mg of the product of Preparation Z3 and 1.3 μl of 2.5M n-butyl lithium (hexane) in 20 ml of tetrahydrofuran there was obtained 753 mg of the desired product.

5.
6-(5-fluorobenzothiazol-2-yl-trans-ethenyl)chroman-4-one

Following the procedure of Preparation Y7, 750 mg of the product of Preparation Z4 and 5 ml of 2N hydrochloric acid in 10 ml of tetrahydrofuran gave 513 mg of the titled product as a solid, m.p. 197°-199° C.

6.
4-hydroxy-6-(5-fluorobenzothiazol-2-yl-trans-ethenyl)-chroman

Starting with 489 mg of the product of Preparation Z5 and 57 mg of sodium borohydride in 10 ml of methanol and 20 ml of dry tetrahydrofuran and employing the procedure of Preparation G3, 446 mg of the titled product was obtained, m.p. 184°-186° C.

PREPARATION AA 1-(4-[3-Aminophenylmethoxylphenyl)-2-methyl-1H-imidazo[4,5-c]pyridine Using the procedure of Example 3, 500 mg of 3-aminobenzyl alcohol, 1.01 g of the product of Preparation A, 1.17 g of triphenylphosphine and 848 mg of diethyl azodicarboxylate in 20 ml of dry tetrahydrofuran gave 370 mg of the desired product, m.p. 182°-185° C.

PREPARATION BB

5-Fluorobenzothiazole-2-carboxylic Acid 1. 5-fluorobenzothiazole-2-carboxaldehyde To a stirred solution of 36 g of 5-fluorobenzothiazole in 100 ml of diethyl ether cooled to −70° C. was added dropwise over a 5 minute period 9.4 ml of a 2.5M solution of n-butyl lithium in hexane. The reaction mixture was allowed to warm to −50° C. for one hour and was then cooled to −78° C. Dry dimethylformamide (2.8 ml) was added dropwise and the reaction mixture allowed to warm to room temperature over a period of two hours. The reaction was diluted with 300 ml of diethyl ether and washed with 1N hydrochloric acid (1×40 ml), water (1×40 ml), a saturated sodium bicarbonate solution (1×40 ml) and dried over magnesium sulfate. The solvent was removed and the residual product flash chromatographed on silica (50% ethyl acetate—hexane; v:v) to give 24.7 g of the titled product, m.p. 105°-107° C.

2. 5-fluorobenzothiazole-2-carboxylic acid

To a solution of 200 mg of the product of Preparation BB1 in 20 ml of ethanol was added 256 mg of silver oxide followed by 0.6 ml of 2M aqueous sodium hydroxide solution and the resulting reaction mixture stirred at room temperature for 4 hours. The solids were filtered and the filtrate concentrated in vacuo. The residue was dissolved in 100 ml of water and extracted with diethyl ether. The aqueous was made slightly acidic with 1N hydrochloric acid and extracted with chloroform (7×100 ml) . The extracts were combined, dried and concentrated to give 62 mg of product, m.p. 123° C. (dec).

PREPARATION CC 3-(5-Fluorobenzothiazol-2-ylmethoxy) phenylglycol

A mixture of 750 mg of methyl 3-(5-fluorobenzothiazol-2-ylmethoxy)mandelate and 190 mg of sodium borohydride in 10 ml of methanol was stirred at room temperature for 4 hours. The solvent was removed in vacuo and the residue treated with water and extracted With ethyl acetate. The extracts were combined, dried over sodium sulfate and concentrated to give 700 mg of the titled product, m.p. 115° C.

PREPARATION DD 3-(6-Chloro-1,3-benzthiazin-2-yl-transethenyl)benzyl alcohol 1. 3-(6-chloro-1,3-benzthiazin-2-yl-transethenyl)benzyl alcohol t-butyldimethylsilyl ether A mixture of 1.08 g of 2-methyl-6-chloro-1,3-benzthiazine 1.51 g of 3-formylbenzyl alcohol t-butyldimethylsilyl ether and 5 drops of piperidine in 60 ml of benzene was heated to reflux in a Dean-Stark trap for 1 hour. An additional 5 drops of piperidine were added and the refluxing continued from 30 hours. The mixture was diluted with 400 ml of ethyl acetate and washed with water (1×40 ml) and brine (1×40 ml). The organic layer was dried over magnesium sulfate and concentrated to 2 g of crude product which was chromatographed on silica gel using 5% ethyl acetate in hexane (v:v), 188 mg, m.p. 58°-60° C.

2. 3-(6-chloro-1,3-benzthiazin-2-yl-transethenyl)benzyl alcohol

Starting with 173 mg of the product of Preparation DD1 and 0.5 ml of tetrabutylammonium fluoride and using the procedure of Preparation GG3 gave 39 mg of the desired product, m.p. 143°-145° C.

PREPARATION EE 3-(5-Fluorobenzothiazol-2-ylmethylsulfinyl)benzyl alcohol and 3-(5-fluorobenzothiazol-2-ylmethylsulfonyl)benzyl alcohol To stirred solution of 822 mg of 3-(5-fluorobenzothiazol-2-ylmethylthio)benzyl alcohol in 20 ml of methylene chloride cooled to 0° C. was added 929 mg of 50-60% m-chloroperbenzoic acid and the reaction mixture stirred at 0° C. for one hour. The reaction was diluted with 400 ml of ethyl acetate and extracted with a saturated solution of sodium bicarbonate (2×40 ml), water (1×40 ml) and a brine solution (1×40 ml). The organic phase was dried over magnesium sulfate and concentrated to give 2 g of solid material which on flash chromatographing on silica gel gave (2.5% methanol in methylene chloride; v:v) 691 mg of the orange sulfone, m.p. 128°-130° C. and 188 mg of the sulfoxide as a white solid, m.p. 145°-147° C.

PREPARATION FF 1-(2-Fluoro-4-hydroxyphenyl)-2-methyl-1H-imidazo[4,5-c]pyridine 1. 2-nitro-4-(2-fluoro-4-hydroxyphenylamino)pyridine To a suspension of 2.86 g of 2-fluoro-4-hydroxyaniline and 2.08 g of sodium bicarbonate in 25 ml of ethanol was added dropwise 3.93 g of 3-nitro-4-chloropyridine in 25 ml of ethanol over a period of 15 minutes. The reaction was stirred overnight at room temperature and was then heated to reflux for 8 hours. The precipitate was filtered, washed with ethanol and water, and dried, 5.28 g. The product was purified by chromatographing on 600 g of silica gel. A small sample was recrystallized from isopropanol m.p. 275°-276° C.

2. 2-amino-4-(2-fluoro-4-hydroxyphenylamino)pyridine

A mixture of 3.73 g of the product of Preparation FF1 and 2 g of 10% palladium on charcoal in 100 ml of tetrahydrofuran and 100 ml of methanol was shaken in an atmosphere of hydrogen at room temperature and an initial pressure of 30 p.s.i. After 30 minutes the spent catalyst was filtered and the filtrate concentrated to dryness, 3.19 g. A sample was recrystallized from isopropanol-hexane, m.p. 209° C. (dec).

3. 1-(2-fluoro-4-acetoxyphenyl) -2-methyl-1H-imidazo [4,5-c]pyridine

Acetic anhydride (75 ml) containing 3.09 g of the product of Preparation FF2 was heated to reflux under nitrogen for 4 hours. The reaction was cooled to room temperature and concentrated in vacuo to dryness. The residue was chromatographed on 350 g of silica gel using 4% methanol in methylene chloride (v:v) to give 2.30 g of a product as a white foam and 1.96 g of an off-white foam. The latter material was used in the next reaction step without further purification.

4. 1-(2-fluoro-4-hydroxyphenyl) -2-methyl-1H-imidazo[4,5-c]pyridine

To 20 ml of water and 80 ml of methanol was added 1.92 g of the product of Preparation FF3 and 538 mg of sodium hydroxide and reaction stirred at room temperature for 3 hours under nitrogen. The reaction was poured into 1 l of water and the pH adjusted to 6-7 with 1N hydrochloric acid. After chilling in ice, the precipitate was filtered and dried, 1.07 g. A small sample was recrystallized from methanol, m.p. 294° C.

PREPARATION GG 1-(5-Fluorobenzothiazol-2-yl)-2-(m-hydroxymethylphenyl)cyclopropane 1. 3-(5-fluorobenzothiazol-2-yl-trans-ethenyl)benzyl alcohol t-butyldimethylsilyl ether To 100 ml of dimethylformamide containing 2.0 g of 3-(5-fluorobenzothiazol-2-yl-trans-ethenyl)benzyl alcohol and 1.19 g of imidazole was added 1.37 g of t-butyldimethylsilyl chloride and the reaction mixture stirred overnight under nitrogen at room temperature. After 48 hours of reaction time, the mixture was poured into 500 ml of ethyl acetate and washed with water (3×150 ml), a 1N hydrochloric acid solution (2×150 ml), water (1×200 ml) and a brine solution (1×200 ml) The organic layer was separated, dried over sodium sulfate and concentrated to a white solid. The residue was recrystallized from ethyl acetate—hexane, 1.57 g, m.p. 91°-93° C.

2. 1-(5-fluorobenzothiazol-2-yl) -2-(m-t-butyldimethylsilyloxymethyl]phenyl)cyclopropane To 160 mg of 60% sodium hydride washed free of oil using pentane was added 867 of trimethylsulfoxonium iodide and the flask purged with nitrogen and evacuated several times. Dimethylsulfoxide (5 ml) was added and the reaction mixture stirred 15-20 minutes at room temperature. The product of Preparation GG1 (1.5 g) in 10 ml of warm dimethylsulfoxide was added to the rest of the reagents chilled to 20° C. The resulting yellow suspension was stirred at room temperature for 21 hours and was then added to 200 ml of water. The aqueous was extracted with ethyl acetate which was then washed with water (3×100 ml) and a brine solution (1×100 ml). The organic phase was dried over sodium sulfate and concentrated to give 1.74 g of a yellow oil. The residue was chromatographed on 300 g of silica gel using 5% ethyl acetate in hexane (v:v) to give 560 mg of product. Rechromatographing gave 284 mg of pure intermediate, m.p. 56°-58° C.

3. 1-(5-fluorobenzothiazol-2-yl) -2-(m-hydroxymethylphenyl) cyclopropane

To a solution of 252 mg of the product of Preparation GG2 in 8 ml of tetrahydrofuran cooled to 0° C. under nitrogen was added tetrabutylammonium fluoride dropwise. The reaction was allowed to warm to room temperature and was then diluted with ethyl acetate and washed with water and a brine solution, and dried over sodium sulfate. Removal of the solvent gave 230 mg of solid which was chromatographed on 100 g of silica gel (5% ethyl acetate in methylene chloride, v:v) to give 153 mg of a clear oil.

We claim:

1. A compound of the formula

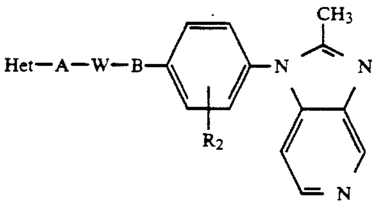

and a pharmaceutically acceptable acid addition salt thereof, wherein Het is

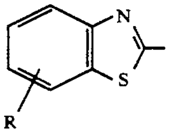, 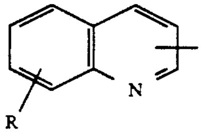,

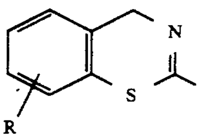, 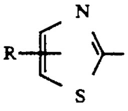,

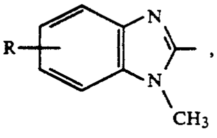, 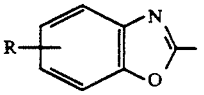,

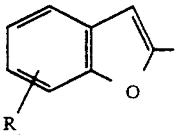 or 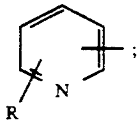;

A is $—CH_2O—$, 'C≡C—, —CH=CH—, $—C(CH_3)—CH—$, $—CH_2NH—$, $—NHCH_2—$, $—(CH_2)_n—$, —O—, $—CH_2S(O)_m—$, —NHCO, —CONH— or cycloalkylene having three to six carbon atoms;

W is

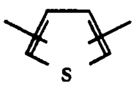, 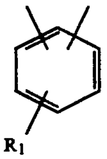, 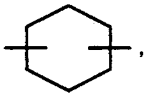,

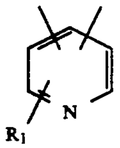, 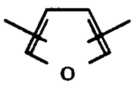, 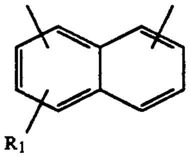,

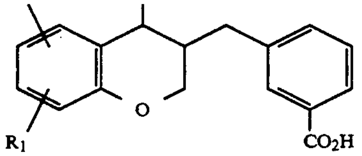,

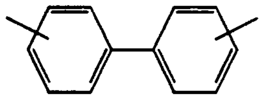,

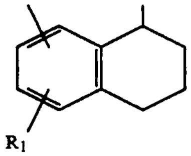 or 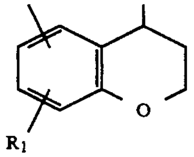;

B is $—NHCH_2—$, $—CH_2O—$, $—CH(CH_3)O—$, —O—, $—(CH_2)_2—$, $—OCH_2—$,

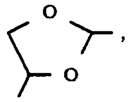, 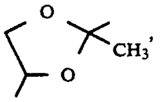

$—CH_2OCH_2—$ or —NHCO—;

n is an integer of 1 to 2; m is an integer of 0 to 2; R is hydrogen, fluoro, difluoro, chloro, dichloro, methyl, methoxy or trifluoromethyl; and $R_1$ and $R_2$ are each hydrogen, fluoro, chloro, methyl, methoxy, acetyl, nitro, amino, carboxy, trifluoromethylsulfonylamino or trifluoromethyl with the proviso that when B is —O—, w is

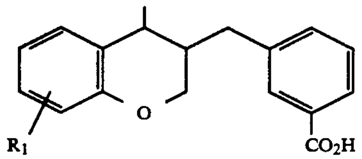

-continued

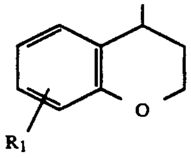 or 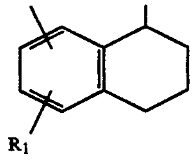.

2. A compound of claim 1, wherein Het is

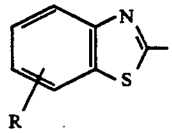 or 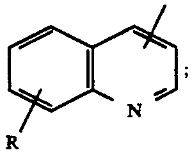;

A is $—(CH_2)_2—$, $—CH_2O—$ or —CH=CH—; W is

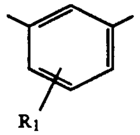 or 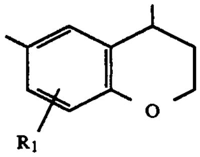; B is $—CH_2O—$, $—OCH_2—$, —O— or $—CH(CH_3)—O—$; and $R_1$ and $R_2$ are each hydrogen.

3. The compound of claim 2, wherein Het is

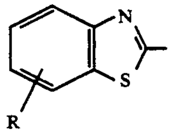

where R is 5-fluoro; A is —CH=CH—; W is

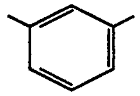;

and B is $—CH_2O—$.

4. The compound of claim 2, wherein Het is

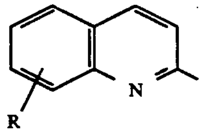, where R is 6-fluoro; A is —CH=CH—;

W is 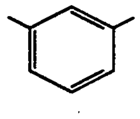;

and B is $—CH_2O—$.

5. The compound of claim 2, whrein Het is

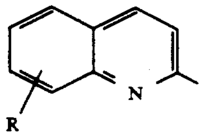

where R is 7-chloro; A is —CH=CH—; W is

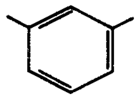
;

and B is —$CH_2O$—.

6. The compound of claim 2, wherein Het is

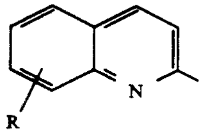

where R is 6-fluoro; A is —$CH_2O$—; W is

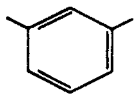
;

and B is —$OCH_2$—.

7. The compound of claim 2, wherein Het is

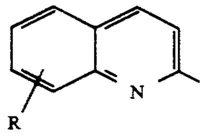

where R is 6-fluoro; A is —CH=CH—; W is

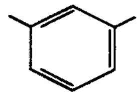
;

and B is —$CH(CH_3)O$—.

8. The compound of claim 2, wherein Het is

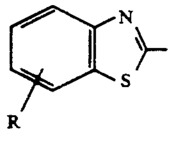

where R is 5-fluoro; A is —$CH_2O$; W is

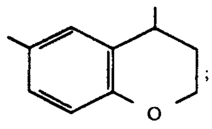
;

and B is —O—.

9. The compound of claim 2, wherein Het is

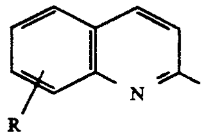
, where R is hydrogen; A is —$CH_2O$—; W is

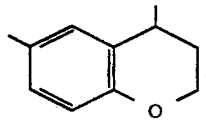
;

and B is —O—.

10. The compound of claim 2, wherein Het is

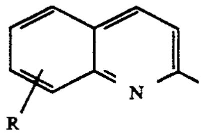
;

where R is 6-fluoro; A is —$CH_2O$—; W is

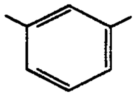
;

and B is —$OCH_2$—.

11. The compound of claim 2, wherein het is

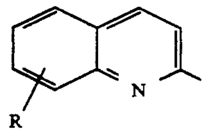

where R is 7-chloro; A is —CH=CH—; W is

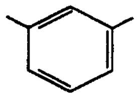
;

and B is —$CH(CH_3)O$—.

12. The compound of claim 2, wherein Het is

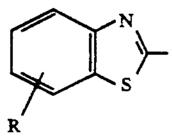

where R is 5-fluoro; A is —CH=CH—; W is

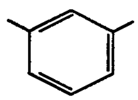
;

and B is —CH(CH₃)O—.

13. The compound of claim 2, wherein Het is

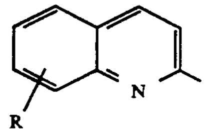

where R is 7-chloro; A is —$CH_2O$—; W is

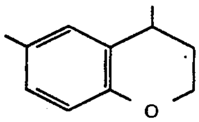
;

and B is —O—.

14. The compound of claim 2, wherein Het is

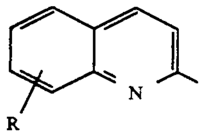

where R is 6-fluoro; A is —$CH_2O$—; W is

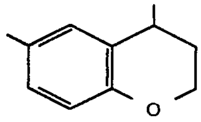
;

and B is —O—.

15. The compound of claim 2, wherein Het is

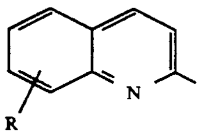

where R is 7-chloro; A is —$CH_2O$—; W is

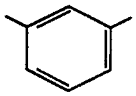
;

and B is —$CH_2O$—.

16. The compound of claim 2, wherein Het is

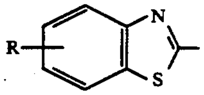

where R is 5-fluoro; A is —$(CH_2)_2$—; W is

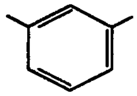
;

and B is —$CH_2O$—.

17. The compound of claim 2, wherein Het is

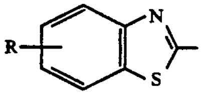

where R is 5,6-difluoro; A is —$CH_2O$—; W is

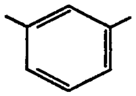
;

and B is —$CH_2O$—.

18. The compound of claim 2, wherein Het is

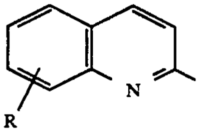

where R is 7-chloro; A is —$(CH_2)_2$—; W is

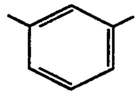
;

and B is —$CH_2O$.

19. The compound of claim 2, wherein Het is

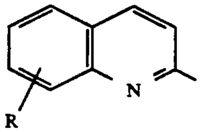
, where R is 6-fluoro; A is —$CH_2O$—; W is

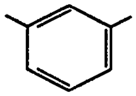
;

and B is —$CH_2O$—.

20. The compound of claim 2, wherein Het is

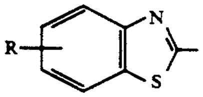

where R is 6-fluoro; A is $—CH_2O—$; W is

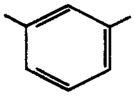
;

and B is $—CH_2O—$.

21. A method of inhibiting platelet activating factor and blocking leukotriene D4 receptor in a mammal in need of such treatment which comprises administering to said mammal a platelet activating factor inhibiting and leukotriene D4 receptor blocking amount of a compound according to claim 1.

22. A method of claim 21 wherein the mammal is a human suffering from asthma, said compound administered to prevent or relieve the symptoms of said asthma.

23. A method of claim 21 wherein the mammal is a human suffering from arthritis, said compound administered to prevent or relieve the symptoms of said arthritis.

24. A method of claim 21 wherein the mammal is a human suffering from psoriasis, said compound administered to prevent or relieve the symptoms of said psoriasis.

25. A method of claim 21 wherein the mammal is a human suffering from gastrointestinal distress, said compound administered to prevent or relieve gastrointestinal ulcers.

26. A method of claim 21 wherein the mammal is a human suffering from cardiovascular disease, said compound administered to prevent or relieve myocardial infarction.

27. A method of claim 21 wherein the mammal is a human suffering from cardiovascular disease, said compound administered to prevent or relieve stroke.

28. A method of claim 21, wherein the mammal is a human suffering from shock, said compound administered to prevent or relieve the symptoms of said shock.

29. A pharmaceutical composition for administration to a mammal which comprises a platelet activating factor inhibiting and leukotriene D4 receptor blocking amount of a compound according to claim 1 and a pharmaceutically acceptable carrier.

* * * * *

UNITED STATES PATENT AND TRADEMARK OFFICE
CERTIFICATE OF CORRECTION

PATENT NO. : 5,322,847

DATED : June 21, 1994

INVENTOR(S) : Anthony Marfat et al.

It is certified that error appears in the above-identified patent and that said Letters Patent is hereby corrected as shown below:

At column 1, line 22, following the word "prevention", delete the word "to";

At column 3, line 32, insert a comma after the word "methyl"; and delete "=".

At column 3, line 32, "trifluoromethy" should read --trifluoromethyl--.

Signed and Sealed this

Twenty-ninth Day of November, 1994

Attest:

BRUCE LEHMAN

*Attesting Officer* *Commissioner of Patents and Trademarks*